United States Patent [19]

Gossen et al.

[11] Patent Number: 5,464,758
[45] Date of Patent: Nov. 7, 1995

[54] TIGHT CONTROL OF GENE EXPRESSION IN EUCARYOTIC CELLS BY TETRACYCLINE-RESPONSIVE PROMOTERS

[76] Inventors: Manfred Gossen, Ringstrasse 33, D-69115 Heidelberg; Hermann Bujard, Remlerstrasse 9, D-69120 Heidelberg, both of Germany

[21] Appl. No.: 76,726

[22] Filed: Jun. 14, 1993

[51] Int. Cl.[6] .............................. C12N 15/09; C12N 5/10; C12N 15/11; C12N 15/62
[52] U.S. Cl. .................. 435/69.1; 435/70.1; 435/172.3; 435/240.2; 435/240.4; 435/320.1; 536/23.4; 536/24.1
[58] Field of Search .......................... 435/172.3, 240.2, 435/240.4, 320.1, 69.1, 70.1; 536/23.2, 23.4, 23.5, 24.1

[56] References Cited

FOREIGN PATENT DOCUMENTS 0519336 12/1992 European Pat. Off. ........ C12N 15/67

OTHER PUBLICATIONS

Clark et al., in: *Experimental Biology* (W. H. Freeman & Co., N.Y.), pp. 97–103 (1977).
Derwent World Patents Index Abstract, WPI Acc. No.: 92-425576/52.
Altschmied, L. et al., "A threonine to alanine exchange at position 40 of Tet repressor alters the recognition of the sixth base pair of tet operator from GC to AT", *EMBO J.* 7:4011–4017, (1988).
Baim, S. et al., "A Chimeric Mammalian Transactivator Based on the Lac Repressor that is Regulated by Temperature and Isopropyl Beta–D–Thiogalactopyranoside", *Procl. Natl. Acad. Sci. USA* 88:5072–5076 (Jun. 1991).
Barkley & Bourgeois in *The Operon*, "Repressor Recognition of Operator and Effectors", Miller, J., Reznikoff, W. (eds.), Cold Spring Harbor Laboratory, Cold Spring Harbor: N.Y., pp. 177–220, (1980).
Boshart, M. et al., "A Very Strong Enhancer is Located Upstream of an Immediate Early Gene of Human Cytomegalovirus", *Cell* 41:521–530 (Jun. 1985).
Courey, A., Tjian, R., "Analysis of Sp1 in vivo Reveals Multiple Transcriptional Domains, Including a Novel Glutamine–Rich Activation Motif", *Cell* 55:887–898 (Dec. 1988).
Deuschle, U. et al., "Regulated Expression of Foreign Genes in Mammalian Cells Under the Control of Coliphage T3 RNA Polymerase and Lac Repressor", *Proc. Natl. Acad Sci. USA* 86:5400–5404 (Jul. 1989).
DeWet, J. et al., "Firefly Luciferase Gene: Structure and Expression in Mammalian Cells", *Mol. Cell. Biol.* 7:725–737 (Feb. 1987).
Gatz, C. et al., "Regulation of a Modified CaMV 35S Promoter by the Tn10–encoded Tet Repressor in Transgenic Tobacco", *Mol. Gen. Genet.* 227:229–237 (1991).
Gatz, C. et al., "Tn10–encoded Tet Repressor Can Regulate an Operator–Containing Plant Promoter", *Proc. Natl. Acad. Sci. USA* 85:1394–1397 (Mar. 1988).
Gill, G., Ptashne, M., "Negative Effect of the Transcriptional Activator GAL4", *Nature (London)* 334:721–724 (Aug. 1988).
Giniger, E., Ptashne, M., "Transcription in Yeast Activated by a Putative Amphipathic Alpha Helix Linked to a DNA Binding Unit", *Nature* 330:670–672 (Dec. 1987).
Gossen, M. et al., "Tight Control of Gene Expression in Mammalian Cells by Tetracycline–Responsive Promoters", *Proc. Natl. Acad. Sci. USA* 89(12):5547–5551 (Jun. 1992).
Hillen & Wissman, "Topics in Molecular & Structural Biology, in Protein–Nucleic Acid Interaction: Tet repressor–tet operator interaction", Saeger & Heinemann (eds.), MacMillan, London, 1989, vol. 10, pp. 143–162.
Labow, M. et al., "Conversion of the Lac Repressor into an Allosterically Regulated Transcriptional Activator for Mammalian Cells", *Mol. Cell. Biol.* 10:3343–3356 (Jul. 1990).
Mermod, M. et al., "The Proline–Rich Transcriptional Activator of CTF/NF–I is distinct from the Replication and DNA Binding Domain", *Cell* 58:741–753 (Aug. 1989).
Nordeen, S., "Luciferase Reporter Gene Vectors for Analysis of Promoters and Enhancers", *Biotechniques* 6:454–457 (1988).
Postle, K. et al., "Nucleotide Sequence of the Repressor Gene of the TN10 Tetracycline Resistant Determinant", *Nucl. Acids Res.* 12:4849–4863 (1984).
Seeburg, P. et al., "The $GABA_A$ Receptor Family: Molecular and Functional Diversity", *Cold Spring Harbor Symp. Quant. Biol.* 55:29–40 (1990).
Southern, P., Berg, P., "Transformation of Mammalian Cells to Antibiotic Resistance with a Bacterial Gene Under Control of the SV40 Early Region Promoter", *J. Mol. Appl. Genet.* 1:327–341 (1982).
Takahashi, M. et al., "Kinetic and Equilibrium Characterization of the Tet Repressor–Tetracycline Complex by Fluorescence Measurements", *J. Mol. Biol.* 187:341–348 (1986).
Tanaka, M., Herr, W., "Differential Transcriptional Acivation by Oct–1 and Oct–2: Interdependent Activation Domains Induce Oct–2 Phosphorylation", *Cell* 60:375–386 (Feb. 1990).
Tovar, K. et al., "Identification and Nucleotide Sequence of the Class E Tet Regulatory Elements and Operator and Inducer Binding of the Encoded Purified Tet Repressor", *Mol. Gen. Genet.* 215:76–80 (1988).

(List continued on next page.)

*Primary Examiner*—Richard A. Schwartz
*Assistant Examiner*—Philip W. Carter
*Attorney, Agent, or Firm*—Sterne, Kessler, Goldstein & Fox

[57] ABSTRACT

A first polynucleotide molecule coding for a transactivator fusion protein comprising the tet repressor and a protein capable of activating transcription in eucaryotes. A second polynucleotide molecule coding for a protein, wherein said polynucleotide is operably linked to a minimal promoter operably linked to at least one tet operator sequence is also disclosed. A method to regulate the expression of a protein coded for by a polynucleotide, by cultivating the eucaryotic cell of the invention in a medium comprising tetracycline or a tetracycline analogue is also disclosed. Kits containing the polynucleotide molecules are also disclosed.

19 Claims, 13 Drawing Sheets

OTHER PUBLICATIONS

Triezenberg, S. et al., "Functional Dissection of VP16, the Trans–Activator of Herpes Simpex Virus Immediate Early Gene Expression", *Genes Dev.* 2:718–729 (1988).

Unger, B. et al., "Nucleotide Sequence of the Gene, Protein Purification and Characterization of the p SC101–encoded Tetracycline Resistant Gene Repressor", *Gene* 31:103–108 (1984).

Unger, B. et al., "Nucleotide Sequence of the Repressor Gene of the RA1 Tetracycline Resistant Determinant: Structural and Functional Comparison with Three Related Tet Repressor Genes", *Nucl. Acids Res.* 12:7693–7703 (1984).

Waters, S. et al., "The Tetracycline Resistance Determinants of RP1 and Tn1721: Nucleotide Sequence Analysis", *Nucl. Acids Res.* 11:6089–6105 (1983).

Wyborski, D., Short, J., "Analysis of Inducers of the *E. coli* Lac Repressor System in Mammalian Cells and Whole Animals", *Nucleic Acids Res* 19:4657–4653 (1991).

```
1/1                                     31/11
ATG TCT AGA TTA GAT AAA AGT AAA GTG ATT AAC AGC GCA TTA GAG CTG CTT AAT GAG GTC
Met Ser Arg Leu Asp Lys Ser Lys Val Ile Asn Ser Ala Leu Glu Leu Leu Asn Glu Val
61/21                                   91/31
GGA ATC GAA GGT TTA ACA ACC CGT AAA CTC GCC CAG AAG CTA GGT GTA GAG CAG CCT ACA
Gly Ile Glu Gly Leu Thr Thr Arg Lys Leu Ala Gln Lys Leu Gly Val Glu Gln Pro Thr
121/41                                  151/51
TTG TAT TGG CAT GTA AAA AAT AAG CGG GCT TTG CTC GAC GCC TTA GCC ATT GAG ATG TTA
Leu Tyr Trp His Val Lys Asn Lys Arg Ala Leu Leu Asp Ala Leu Ala Ile Glu Met Leu
181/61                                  211/71
GAT AGG CAC CAT ACT CAC TTT TGC CCT TTA GAA GGG GAA AGC TGG CAA GAT TTT TTA CGT
Asp Arg His His Thr His Phe Cys Pro Leu Glu Gly Glu Ser Trp Gln Asp Phe Leu Arg
241/81                                  271/91
AAT AAG GCT AAA AGT TTT AGA TGT GCT TTA CTA AGT CAT CGC GAT GGA GCA AAA GTA CAT
Asn Lys Ala Lys Ser Phe Arg Cys Ala Leu Leu Ser His Arg Asp Gly Ala Lys Val His
301/101                                 331/111
TTA GGT ACA CGG CCT ACA GAA AAA CAG TAT GAA ACT CTC GAA AAT CAA TTA GCC TTT TTA
Leu Gly Thr Arg Pro Thr Glu Lys Gln Tyr Glu Thr Leu Glu Asn Gln Leu Ala Phe Leu
361/121                                 391/131
TGC CAA CAA GGT TTT TCA CTA GAG AAT GCA TTA TAT GCA CTC AGC GCT GTG GGG CAT TTT
Cys Gln Gln Gly Phe Ser Leu Glu Asn Ala Leu Tyr Ala Leu Ser Ala Val Gly His Phe
421/141                                 451/151
ACT TTA GGT TGC GTA TTG GAA GAT CAA GAG CAT CAA GTC GCT AAA GAA GAA AGG GAA ACA
Thr Leu Gly Cys Val Leu Glu Asp Gln Glu His Gln Val Ala Lys Glu Glu Arg Glu Thr
481/161                                 511/171
CCT ACT ACT GAT AGT ATG CCG CCA TTA TTA CGA CAA GCT ATC GAA TTA TTT GAT CAC CAA
Pro Thr Thr Asp Ser Met Pro Pro Leu Leu Arg Gln Ala Ile Glu Leu Phe Asp His Gln
541/181                                 571/191
GGT GCA GAG CCA GCC TTC TTA TTC GGC CTT GAA TTG ATC ATA TGC GGA TTA GAA AAA CAA
Gly Ala Glu Pro Ala Phe Leu Phe Gly Leu Glu Leu Ile Ile Cys Gly Leu Glu Lys Gln
601/201                                 631/211
CTT AAA TGT GAA AGT GGG TCC GCG TAC AGC CGC GCG CGT ACG AAA AAC AAT TAC GGG TCT
Leu Lys Cys Glu Ser Gly Ser Ala Tyr Ser Arg Ala Arg Thr Lys Asn Asn Tyr Gly Ser
661/221                                 691/231
```

FIG.4A

```
ACC ATC GAG GGC CTG CTC GAT CTC CCG GAC GAC GAC GCC CCC GAA GAG GCG GGG CTG GCG
Thr Ile Glu Gly Leu Leu Asp Leu Pro Asp Asp Asp Ala Pro Glu Glu Ala Gly Leu Ala
721/241                              751/251
GCT CCG CGC CTG TCC TTT CTC CCC GCG GGA CAC ACG CGC AGA CTG TCG ACG GCC CCC CCG
Ala Pro Arg Leu Ser Phe Leu Pro Ala Gly His Thr Arg Arg Leu Ser Thr Ala Pro Pro
781/261                              811/271
ACC GAT GTC AGC CTG GGG GAC GAG CTC CAC TTA GAC GGC GAG GAC GTG GCG ATG GCG CAT
Thr Asp Val Ser Leu Gly Asp Glu Leu His Leu Asp Gly Glu Asp Val Ala Met Ala His
841/281                              871/291
GCC GAC GCG CTA GAC GAT TTC GAT CTG GAC ATG TTG GGG GAC GGG GAT TCC CCG GGT CCG
Ala Asp Ala Leu Asp Asp Phe Asp Leu Asp Met Leu Gly Asp Gly Asp Ser Pro Gly Pro
901/301                              931/311
GGA TTT ACC CCC CAC GAC TCC GCC CCC TAC GGC GCT CTG GAT ATG GCC GAC TTC GAG TTT
Gly Phe Thr Pro His Asp Ser Ala Pro Tyr Gly Ala Leu Asp Met Ala Asp Phe Glu Phe
961/321                              991/331
GAG CAG ATG TTT ACC GAT CCC CTT GGA ATT GAC GAG TAC GGT GGG TAG
Glu Gln Met Phe Thr Asp Pro Leu Gly Ile Asp Glu Tyr Gly Gly AMB
```

FIG.4B

```
1/1                                  31/11
ATG TCT AGA TTA GAT AAA AGT AAA GTG ATT AAC AGC GCA TTA GAG CTG CTT AAT GAG GTC
Met Ser Arg Leu Asp Lys Ser Lys Val Ile Asn Ser Ala Leu Glu Leu Leu Asn Glu Val
61/21                                91/31
GGA ATC GAA GGT TTA ACA ACC CGT AAA CTC GCC CAG AAG CTA GGT GTA GAG CAG CCT ACA
Gly Ile Glu Gly Leu Thr Thr Arg Lys Leu Ala Gln Lys Leu Gly Val Glu Gln Pro Thr
121/41                               151/51
TTG TAT TGG CAT GTA AAA AAT AAG CGG GCT TTG CTC GAC GCC TTA GCC ATT GAG ATG TTA
Leu Tyr Trp His Val Lys Asn Lys Arg Ala Leu Leu Asp Ala Leu Ala Ile Glu Met Leu
181/61                               211/71
GAT AGG CAC CAT ACT CAC TTT TGC CCT TTA GAA GGG GAA AGC TGG CAA GAT TTT TTA CGT
Asp Arg His His Thr His Phe Cys Pro Leu Glu Gly Glu Ser Trp Gln Asp Phe Leu Arg
241/81                               271/91
AAT AAC GCT AAA AGT TTT AGA TGT GCT TTA CTA AGT CAT CGC GAT GGA GCA AAA GTA CAT
Asn Asn Ala Lys Ser Phe Arg Cys Ala Leu Leu Ser His Arg Asp Gly Ala Lys Val His
301/101                              331/111
TTA GGT ACA CGG CCT ACA GAA AAA CAG TAT GAA ACT CTC GAA AAT CAA TTA GCC TTT TTA
Leu Gly Thr Arg Pro Thr Glu Lys Gln Tyr Glu Thr Leu Glu Asn Gln Leu Ala Phe Leu
361/121                              391/131
TGC CAA CAA GGT TTT TCA CTA GAG AAT GCA TTA TAT GCA CTC AGC GCT GTG GGG CAT TTT
Cys Gln Gln Gly Phe Ser Leu Glu Asn Ala Leu Tyr Ala Leu Ser Ala Val Gly His Phe
421/141                              451/151
ACT TTA GGT TGC GTA TTG GAA GAT CAA GAG CAT CAA GTC GCT AAA GAA GAA AGG GAA ACA
Thr Leu Gly Cys Val Leu Glu Asp Gln Glu His Gln Val Ala Lys Glu Glu Arg Glu Thr
481/161                              511/171
CCT ACT ACT GAT AGT ATG CCG CCA TTA TTA CGA CAA GCT ATC GAA TTA TTT GAT CAC CAA
Pro Thr Thr Asp Ser Met Pro Pro Leu Leu Arg Gln Ala Ile Glu Leu Phe Asp His Gln
541/181                              571/191
GGT GCA GAG CCA GCC TTC TTA TTC GGC CTT GAA TTG ATC ATA TGC GGA TTA GAA AAA CAA
Gly Ala Glu Pro Ala Phe Leu Phe Gly Leu Glu Leu Ile Ile Cys Gly Leu Glu Lys Gln
601/201                              631/211
CTT AAA TGT GAA AGT GGG TCT GAT CCA TCG ATA CAC ACG CGC AGA CTG TCG ACG GCC CCC
Leu Lys Cys Glu Ser Gly Ser Asp Pro Ser Ile His Thr Arg Arg Leu Ser Thr Ala Pro
661/221                              691/231
CCG ACC GAT GTC AGC CTG GGG GAC GAG CTC CAC TTA GAC GGC GAG GAC GTG GCG ATG GCG
Pro Thr Asp Val Ser Leu Gly Asp Glu Leu His Leu Asp Gly Glu Asp Val Ala Met Ala
```

FIG.5A

```
721/241                              751/251
CAT GCC GAC GCG CTA GAC GAT TTC GAT CTG GAC ATG TTG GGG GAC GGG GAT TCC CCG GGT
His Ala Asp Ala Leu Asp Asp Phe Asp Leu Asp Met Leu Gly Asp Gly Asp Ser Pro Gly
781/261                              811/271
CCG GGA TTT ACC CCC CAC GAC TCC GCC CCC TAC GGC GCT CTG GAT ATG GCC GAC TTC GAG
Pro Gly Phe Thr Pro His Asp Ser Ala Pro Tyr Gly Ala Leu Asp Met Ala Asp Phe Glu
841/281                              871/291
TTT GAG CAG ATG TTT ACC GAT GCC CTT GGA ATT GAC GAG TAC GGT GGG TTC TAG
Phe Glu Gln Met Phe Thr Asp Ala Leu Gly Ile Asp Glu Tyr Gly Gly Phe AMB
```

FIG.5B

GAATTCCTCGAGTTTACCACTCCCTATCAGTGATAGAGAAAAGTGAAAGTCGAGTTTACCACTC
CCTATCAGTGATAGAGAAAAGTGAAAGTCGAGTTTACCACTCCCTATCAGTGATAGAGAAAAGT
GAAAGTCGAGTTTACCACTCCCTATCAGTGATAGAGAAAAGTGAAAGTCGAGTTTACCACTCCC
TATCAGTGATAGAGAAAAGTGAAAGTCGAGTTTACCACTCCCTATCAGTGATAGAGAAAAGTGA
AAGTCGAGTTTACCACTCCCTATCAGTGATAGAGAAAAGTGAAAGTCGAGCTCGGTACCCGGGT
CGAGTAGGCGTGTACGGTGGGAGGCCTATATAAGCAGAGCTCGTTTAGTGAACCGTCAGATCGC
CTGGAGACGCCATCCACGCTGTTTTGACCTCCATAGAAGACACCGGGACCGATCCAGCCTCCGC
GG

FIG.6

GAATTCCTCGACCCGGGTACCGAGCTCGACTTTCACTTTTCTCTATCACTGATAGGGAGTGGTA
AACTCGACTTTCACTTTTCTCTATCACTGATAGGGAGTGGTAAACTCGACTTTCACTTTTCTCT
ATCACTGATAGGGAGTGGTAAACTCGACTTTCACTTTTCTCTATCACTGATAGGGAGTGGTAAA
CTCGACTTTCACTTTTCTCTATCACTGATAGGGAGTGGTAAACTCGACTTTCACTTTTCTCTAT
CACTGATAGGGAGTGGTAAACTCGACTTTCACTTTTCTCTATCACTGATAGGGAGTGGTAAACT
CGAGTAGGCGTGTACGGTGGGAGGCCTATATAAGCAGAGCTCGTTTAGTGAACCGTCAGATCGC
CTGGAGACGCCATCCACGCTGTTTTGACCTCCATAGAAGACACCGGGACCGATCCAGCCTCCGC
GG

FIG.7

GAGCTCGACTTTCACTTTTCTCTATCACTGATAGGGAGTGGTAAACTCGACTTTCACTTTTCTC
TATCACTGATAGGGAGTGGTAAACTCGACTTTCACTTTTCTCTATCACTGATAGGGAGTGGTAA
ACTCGACTTTCACTTTTCTCTATCACTGATAGGGAGTGGTAAACTCGACTTTCACTTTTCTCTA
TCACTGATAGGGAGTGGTAAACTCGACTTTCACTTTTCTCTATCACTGATAGGGAGTGGTAAAC
TCGACTTTCACTTTTCTCTATCACTGATAGGGAGTGGTAAACTCGAGATCCGGCGAATTCGAAC
ACGCAGATGCAGTCGGGGCGGCGCGGTCCGAGGTCCACTTCGCATATTAAGGTGACGCGTGTGG
CCTCGAACACCGAG

FIG.8

```
CTCGAGTTTACCACTCCCTATCAGTGATAGAGAAAAGTGAAAGTCGAGTTTACCACTCCCTATC
AGTGATAGAGAAAAGTGAAAGTCGAGTTTACCACTCCCTATCAGTGATAGAGAAAAGTGAAAGT
CGAGTTTACCACTCCCTATCAGTGATAGAGAAAAGTGAAAGTCGAGTTTACCACTCCCTATCAG
TGATAGAGAAAAGTGAAAGTCGAGTTTACCACTCCCTATCAGTGATAGAGAAAAGTGAAAGTCG
AGTTTACCACTCCCTATCAGTGATAGAGAAAAGTGAAAGTCGAGCTCGGTACCCGGGTCGAGTA
GGCGTGTACGGTGGGAGGCCTATATAAGCAGAGCTCGTTTAGTGAACCGTCAGATCGCCTGGAG
ACGCCATCCACGCTGTTTTGACCTCCATAGAAGACACCGGGACCGATCCAGCCTCCGCGGCCCC
GAATTCGAGCTCGGTACCGGGCCCCCCCTCGAGGTCGACGGTATCGATAAGCTTGATATCGAAT
TCCAGGAGGTGGAGATCCGCGGGTCCAGCCAAACCCCACACCCATTTTCTCCTCCCTCTGCCCC
TATATCCCGGCACCCCCTCCTCCTAGCCCTTTCCCTCCTCCCGAGAGACGGGGGAGGAGAAAAG
GGGAGTTCAGGTCGACATGACTGAGCTGAAGGCAAAGGAACCTCGGGCTCCCCACGTGGCGGGC
GGCGCGCCCTCCCCCACCGAGGTCGGATCCCAGCTCCTGGGTCGCCCGGACCCTGGCCCCTTCC
AGGGGAGCCAGACCTCAGAGGCCTCGTCTGTAGTCTCCGCCATCCCCATCTCCCTGGACGGGTT
GCTCTTCCCCCGGCCCTGTCAGGGGCAGAACCCCCAGACGGGAAGACGCAGGACCCACCGTCG
TTGTCAGACGTGGAGGGCGCATTTCCTGGAGTCGAAGCCCCGGAGGGGGCAGGAGACAGCAGCT
CGAGACCTCCAGAAAAGGACAGCGGCCTGCTGGACAGTGTCCTCGACACGCTCCTGGCGCCCTC
GGGTCCCGGCAGAGCCACGCCAGCCCTGCCACCTGCGAGGCCATCAGCCCGTGGTGCCTGTTT
GGCCCCGACCTTCCCGAAGACCCCCGGGCTGCCCCCGCTACCAAAGGGGTGTTGGCCCCGCTCA
TGAGCCGACCCGAGGACAAGGCAGGCGACAGCTCTGGGACGGCAGCGGCCCACAAGGTGCTGCC
CAGGGGACTGTCACCATCCAGGCAGCTGCTGCTCCCTCCTCTGGGAGCCCTCACTGGCCGGCA
GTGAAGCCATCCCCGCAGCCCGCTGCGGTGCAGGTAGACGAGGAGGACAGCTCCGAATCCGAGG
GCACCGTGGGCCCGCTCCTGAAGGGCCAACCTCGGGCACTGGGAGGCACGGCGGCCGGAGGAGG
AGCTGCCCCCGTCGCGTCTGGAGCGGCCGCAGGAGGCGTCGCCCTTGTCCCCAAGGAAGATTCT
CGCTTCTCGGCGCCCAGGGTCTCCTTGGCGGAGCAGGACGCGCCGGTGGCGCCTGGGCGCTCCC
CGCTGGCCACCTCGGTGGTGGATTTCATCCACGTGCCCATCCTGCCTCTCAACCACGCTTTCCT
GGCCACCCGCACCAGGCAGCTGCTGGAGGGGGAGAGCTACGACGGCGGGGCCGCGGCCGCCAGC
CCCTTCGTCCCGCAGCGGGGCTCCCCCTCTGCCTCGTCCACCCCTGTGGCGGGCGGCGACTTCC
CCGACTGCACCTACCCGCCCGACGCCGAGCCCAAAGATGACGCGTTCCCCCTCTACGGCGACTT
CCAGCCGCCCGCCCTCAAGATAAAGGAGGAGGAAGAAGCCGCCGAGGCCGCGGCGCGCTCCCCG
CGTACGTACCTGGTGGCTGGTGCAAACCCCGCCGCCTTCCCGGACTTCCAGCTGGCAGCGCCGC
CGCCACCCTCGCTGCCGCCTCGAGTGCCCTCGTCCAGACCCGGGAAGCGGCGGTGGCGGCCTC
CCCAGGCAGTGCCTCCGTCTCCTCCTCGTCCTCGTCGGGGTCGACCCTGGAGTGCATCCTGTAC
AAGGCAGAAGGCGCGCCGCCCCAGCAGGGCCCCTTCGCGCCGCTGCCCTGCAAGCCTCCGGGCC
CCGGCGCCTGCCTGCTCCCGCGGGACGGCCTGCCCTCCACCTCCGCCTCGGGCGCAGCCGCCGG
GGCCGCCCCTGCGCTCTACCCGACGCTCGGCCTCAACGGACTCCCGCAACTCGGCTACCAGGCC
GCCGTGCTCAAGGAGGGCCTGCCGCAGGTCTACACGCCCTATCTCAACTACCTGAGGCCGGATT
CAGAAGCCAGTCAGAGCCCACAGTACAGCTTCGAGTCACTACCTCAGAAGATTTGTTTGATCTG
TGGGATGAAGCATCAGGCTGTCATTATGGTGTCCTCACCTGTGGGAGCTGTAAGGTCTTCTTT
AAAAGGGCAATGGAAGGGCAGCATAACTATTTATGTGCTGGAAGAAATGACTGCATTGTTGATA
AAATCCGCAGGAAAAACTGCCCCGGCCTGTCGCCCTTAGAAAAGTGCTGTCAAGCTGGCATGGTCCT
```

FIG.9A

```
TGGACGGCGAAAGTTTAAAAAGTTCAATAAAGTCAGAGTCATGAGAGCACTCGATGCTGTTGCT
CTCCCACAGCCAGTGGGCATTCCAAATGAAAGCCAACGAATCACTTTTTCTCCAAGTCAAGAGA
TACAGTTAATTCCCCCTCTAATCAACCTGTTAATGAGCATTGAACCAGATGTGATCTATGCAGG
ACATGACAACACAAAGCCTGATACCTCCAGTTCTTTGCTGACGAGTCTTAATCAACTAGGCGAG
CGGCAACTTCTTTCAGTGGTAAAATGGTCCAAATCTCTTCCAGGTTTTCGAAACTTACATATTG
ATGACCAGATAACTCTCATCCAGTATTCTTGGATGAGTTTAATGGTATTTGGACTAGGATGGAG
ATCCTACAAACATGTCAGTGGGCAGATGCTGTATTTTGCACCTGATCTAATATTAAATGAACAG
CGGATGAAAGAATCATCATTCTATTCACTATGCCTTACCATGTGGCAGATACCGCAGGAGTTTG
TCAAGCTTCAAGTTAGCCAAGAAGAGTTCCTCTGCATGAAAGTATTACTACTTCTTAATACAAT
TCCTTTGGAAGGACTAAGAAGTCAAAGCCAGTTTGAAGAGATGAGATCAAGCTACATTAGAGAG
CTCATCAAGGCAATTGGTTTGAGGCAAAAAGGAGTTGTTTCCAGCTCACAGCGTTTCTATCAGC
TCACAAAACTTCTTGATAACTTGCATGATCTTGTCAAACAACTTCACCTGTACTGCCTGAATAC
ATTTATCCAGTCCCGGGCGCTGAGTGTTGAATTTCCAGAAATGATGTCTGAAGTTATTGCTGCA
CAGTTACCCAAGATATTGGCAGGGATGGTGAAACCACTTCTCTTTCATAAAAAGTGAATGTCAA
TTATTTTTCAAAGAATTAAGTGTTGTGGTATGTCTTTCGTTTTGGTCAGGATTATGACGTCTCG
AGTTTTTATAATATTCTGAAAGGGAATTCCTGCAGCCCGGGGGATCCACTAGTTCTAGAGGATC
CAGACATGATAAGATACATTGATGAGTTTGGACAAACCACAACTAGAATGCAGTGAAAAAAATG
CTTTATTTGTGAAATTTGTGATGCTATTGCTTTATTTGTAACCATTATAAGCTGCAATAAACAA
GTTAACAACAACAATTGCATTCATTTTATGTTTCAGGTTCAGGGGGAGGTGTGGGAGGTTTTTT
AAAGCAAGTAAAACCTCTACAAATGTGGTATGGCTGATTATGATCCTGCAAGCCTCGTCGTCTG
GCCGGACCACGCTATCTGTGCAAGGTCCCCGGACGCGCGCTCCATGAGCAGAGCGCCCGCCGCC
GAGGCAAGACTCGGGCGGCGCCCTGCCCGTCCCACCAGGTCAACAGGCGGTAACCGGCCTCTTC
ATCGGGAATGCGCGCGACCTTCAGCATCGCCGGCATGTCCCCTGGCGGACGGGAAGTATCAGCT
CGACCAAGCTTGGCGAGATTTTCAGGAGCTAAGGAAGCTAAAATGGAGAAAAAAATCACTGGAT
ATACCACCGTTGATATATCCCAATGGCATCGTAAAGAACATTTTGAGGCATTTCAGTCAGTTGC
TCAATGTACCTATAACCAGACCGTTCAGCTGCATTAATGAATCGGCCAACGCGCGGGGAGAGGC
GGTTTGCGTATTGGGCGCTCTTCCGCTTCCTCGCTCACTGACTCGCTGCGCTCGGTCGTTCGGC
TGCCGGCGAGCGGTATCAGCTCACTCAAAGGCGGTAATACGGTTATCCACAGAATCAGGGGATAA
CGCAGGAAAGAACATGTGAGCAAAAGGCCAGCAAAAGGCCAGGAACCGTAAAAAGGCCGCGTTG
CTGGCGTTTTTCCATAGGCTCCGCCCCCCTGACGAGCATCACAAAAATCGACGCTCAAGTCAGA
GGTGGCGAAACCCGACAGGACTATAAAGATACCAGGCGTTTCCCCCTGGAAGCTCCCTCGTGCG
CTCTCCTGTTCCGACCCTGCCGCTTACCGGATACCTGTCCGCCTTTCTCCCTTCGGGAAGCGTG
GCGCTTTCTCAATGCTCACGCTGTAGGTATCTCAGTTCGGTGTAGGTCCTTCGCTCCAAGCTGG
GCTGTGTGCACGAACCCCCCGTTCAGCCCGACCGCTGCGCCTTATCCGGTAACTATCGTCTTGA
GTCCAACCCGGTAAGACACGACTTATCGCCACTGGCAGCAGCCACTGGTAACAGGATTAGCAGA
GCGAGGTATGTAGGCGGTGCTACAGAGTTCTTGAAGTGGTGGCCTAACTACGGCTACACTAGAA
GGACAGTATTTGGTATCTGCGCTCTGCTGAAGCCAGTTACCTTCGGAAAAAGAGTTGGTAGCTC
TTGATCCGGCAAACAAACCACCGCTGGTAGCGGTGGTTTTTTTGTTTGCAAGCAGCAGATTACG
CGCAGAAAAAAAGGATCTCAAGAAGATCCTTTGATCTTTTCTACGGGGTCTGACGCTCAGTGGA
ACGAAAACTCACGTTAAGGGATTTTGGTCATGAGATTATCAAAAAGGATCTTCACCTAGATCCT
```

FIG.9B

```
TTTAAATTAAAAAATGAAGTTTTAAATCAATCTAAAGTATATATGAGTAAACTTGGTCTGACAGT
TACCAATGCTTAATCAGTGAGGCACCTATCTCAGCGATCTGTCTATTTCGTTCATCCATAGTTG
CCTGACTCCCCGTCGTGTAGATAACTACGATACGGGAGGGCTTACCATCTGGCCCCAGTGCTGC
AATGATACCGCGAGACCCACGCTCACCGGCTCCAGATTTATCAGCAATAAACCAGCCAGCCGGA
AGGGCCGAGCGCAGAAGTGGTCCTGCAACTTTATCCGCCTCCATCCAGTCTATTAATTGTTGCC
GGGAAGCTAGAGTAAGTAGTTCGCCAGTTAATAGTTTGCGCAACGTTGTTGCCATTGCTACAGG
CATCGTGGTGTCACGCTCGTCGTTTGGTATGGCTTCATTCAGCTCCGGTTCCCAACGATCAAGG
CGAGTTACATGATCCCCCATGTTGTGCAAAAAAGCGGTTAGCTCCTTCGGTCCTCCGATCGTTG
TCAGAAGTAAGTTGGCCGCAGTGTTATCACTCATGGTTATGGCAGCACTGCATAATTCTCTTAC
TGTCATGCCATCCGTAAGATGCTTTTCTGTGACTGGTGAGTACTCAACCAAGTCATTCTGAGAA
TAGTGTATGCGGCGACCGAGTTGCTCTTGCCCGGCGTCAATACGGGATAATACCGCGCCACATA
GCAGAACTTTAAAAGTGCTCATCATTGGAAAACGTTCTTCGGGGCGAAAACTCTCAAGGATCTT
ACCGCTGTTGAGATCCAGTTCGATGTAACCCACTCGTGCACCCAACTGATCTTCAGCATCTTTT
ACTTTCACCAGCGTTTCTGGGTGAGCAAAAACAGGAAGGCAAAATGCCGCAAAAAAGGGAATAA
GGGCGACACGGAAATGTTGAATACTCATACTCTTCCTTTTTCAATATTATTGAAGCATTTATCA
GGGTTATTGTCTCATGAGCGGATACATATTTGAATGTATTTAGAAAAATAAACAAATAGGGGTT
CCGCGCACATTTCCCCGAAAAGTGCCACCTGACGTCTAAGAAACCATTATTATCATGACATTAA
CCTATAAAAATAGGCGTATCACGAGGCCCTTTCGTC
```

FIG. 9C

```
CTCGAGTTTACCACTCCCTATCAGTGATAGAGAAAAGTGAAAGTCGAGTTTACCACTCCCTATC
AGTGATAGAGAAAAGTGAAAGTCGAGTTTACCACTCCCTATCAGTGATAGAGAAAAGTGAAAGT
CGAGTTTACCACTCCCTATCAGTGATAGAGAAAAGTGAAAGTCGAGTTTACCACTCCCTATCAG
TGATAGAGAAAAGTGAAAGTCGAGTTTACCACTCCCTATCAGTGATAGAGAAAAGTGAAAGTCG
AGTTTACCACTCCCTATCAGTGATAGAGAAAAGTGAAAGTCGAGCTCGGTACCCGGGTCGAGTA
GGCGTGTACGGTGGGAGGCCTATATAAGCAGAGCTCGTTTAGTGAACCGTCAGATCGCCTGGAG
ACGCCATCCACGCTGTTTTGACCTCCATAGAAGACACCGGGACCGATCCAGCCTCCGCGGCCCC
GAATTCCGGCCACGACCATGACCATGACCCTCCACACCAAAGCATCTGGGATGGCCCTACTGCA
TCAGATCCAAGGGAACGAGCTGGAGCCCCTGAACCGTCCGCAGCTCAAGATCCCCCTGGAGCGG
CCCCTGGGCGAGGTGTACCTGGACAGCAGCAAGCCCGCCGTGTACAACTACCCCGAGGGCGCCG
CCTACGAGTTCAACGCCGCGGCCGCCGCCAACGCGCAGGTCTACGGTCAGACCGGCCTCCCCTA
CGGCCCCGGGTCTGAGGCTGCGGCGTTCGGCTCCAACGGCCTGGGGGGTTTCCCCCCACTCAAC
AGCGTGTCTCCGAGCCCGCTGATGCTACTGCACCCGCCGCCGCAGCTGTCGCCTTTCCTGCAGC
CCCACGGCCAGCAGGTGCCCTACTACCTGGAGAACGAGCCCAGCGGCTACACGGTGCGCGAGGC
CGGCCCGCCGGCATTCTACAGGCCAAATTCAGATAATCGACGCCAGGGTGGCAGAGAAAGATTG
GCCAGTACCAATGACAAGGGAAGTATGGCTATGGAATCTGCCAAGGAGACTCGCTACTGTGCAG
TGTGCAATGACTATGCTTCAGGCTACCATTATGGAGTCTGGTCCTGTGAGGGCTGCAAGGCCTT
CTTCAAGAGAAGTATTCAAGGACATAACGACTATATGTGTCCAGCCACCAACCAGTGCACCATT
GATAAAAACAGGAGGAAGAGCTGCCAGGCCTGCCGGCTCCCGCAAATGCTACGAAGTGGGAATGA
TGAAAGGTGGGATACGAAAAGACCGAAGAGGAGGGAGAATGTTGAAACACAAGCGCCAGAGAGA
TGATGGGGAGGGCAGGGGTGAAGTGGGGTCTGCTGGAGACATGAGAGCTGCCAACCTTTGGCCA
AGCCCGCTCATGATCAAACGCTCTAAGAAGAACAGCCTGGCCTTGTCCCTGACGGCCGACCAGA
TGGTCATGGCCTTGTTGGATGCTGAGCCCCCCATACTCTATTCCGAGTATGATCCTACCAGACC
CTTCAGTGAAGCTTCGATGATGGGCTTACTGACCAACCTGGCAGACAGGGAGCTGGTTCACATG
ATCAACTGGGCGAAGAGGGTGCCAGGCTTTGTGGATTTGACCCTCCATGATCAGGTCCACCTTC
TAGAATGTGCCTGGCTAGAGATCCTGATGATTGGTCTCGTCTGGCGCTCCATGGAGCACCCAGT
GAAGCTACTGTTTGCTCCTAACTTGCTCTTGGACAGGAACCAGGGAAAATGTGTAGAGGGCATG
GTGGAGATCTTCGACATGCTGCTGGCTACATCATCTCGGTTCCGCATGATGAATCTGCAGGGAG
AGGAGTTTGTGTGCCTCAAATCTATTATTTTGCTTAATTCTGGACTGTACACATTTCTGTCCAG
CACCCTGAAGTCTCTGGAAGAGAAGGACCATATCCACCGAGTCCTGGACAAGATCACAGACACT
TTGATCCACCTGATGGCCAAGGCAGGCCTGACCCTGCAGCAGCAGCACCAGCGGCTGGCCCAGC
TCCTCCTCATCCTCTCCCACATCAGGCACATGAGTAACAAAGGCATGGAGCATCTGTACAGCAT
GAAGTGCAAGAACGTGGTGCCCCTCTATGACCTGCTGCTGGAGATGCTGGACGCCCACCGCCTA
CATGCCCCACTAGCCGTGGAGGGGCATCCGTGGAGGAGACGGACCAAAGCCACTTGGCCACTG
CGGGCTCTACTTCATCGCATTCCTTGCAAAAGTATTACATCACGGGGAGGCAGAGGGTTTCCC
TGCCACAGTCTGAGAGCTCCCTGGCGGAATTCGAGCTCGGTACCCGGGGATCCTCTAGAGGATC
CAGACATGATAAGATACATTGATGAGTTTGGACAAACCACAACTAGAATGCAGTGAAAAAAATG
CTTTATTTGTGAAATTTGTGATGCTATTGCTTTATTTGTAACCATTATAAGCTGCAATAAACAA
GTTAACAACAACAATTGCATTCATTTTTATGTTTCAGGTTCAGGGGGAGGTGTGGGAGGTTTTTT
AAAGCAAGTAAAACCTCTACAAATGTGGTATGGCTGATTATGATCCTGCAAGCCTCGTCGTCTG
```

FIG.10A

```
GCCGGACCACGCTATCTGTGCAAGGTCCCCGGACGCGCGCTCCATGAGCAGAGCGCCCGCCGCC
GAGGCAAGACTCGGGCGGCGCCCTGCCCGTCCCACCAGGTCAACAGGCGGTAACCGGCCTCTTC
ATCGGGAATGCGCGCGACCTTCAGCATCGCCGGCATGTCCCCTGGCGGACGGGAAGTATCAGCT
CGACCAAGCTTGGCGAGATTTTCAGGAGCTAAGGAAGCTAAAATGGAGAAAAAAATCACTGGAT
ATACCACCGTTGATATATCCCAATGGCATCGTAAAGAACATTTTGAGGCATTTCAGTCAGTTGC
TCAATGTACCTATAACCAGACCGTTCAGCTGCATTAATGAATCGGCCAACGCGCGGGAGAGGC
GGTTTGCGTATTGGGCGCTCTTCCGCTTCCTCGCTCACTGACTCGCTGCGCTCGGTCGTTCGGC
TGCGGCGAGCGGTATCAGCTCACTCAAAGGCGGTAATACGGTTATCCACAGAATCAGGGGATAA
CGCAGGAAAGAACATGTGAGCAAAAGGCCAGCAAAAGGCCAGGAACCGTAAAAAGGCCGCGTTG
CTGGCGTTTTTCCATAGGCTCCGCCCCCTGACGAGCATCACAAAAATCGACGCTCAAGTCAGA
GGTGGCGAAACCCGACAGGACTATAAAGATACCAGGCGTTTCCCCCTGGAAGCTCCCTCGTGCG
CTCTCCTGTTCCGACCCTGCCGCTTACCGGATACCTGTCCGCCTTTCTCCCTTCGGGAAGCGTG
GCGCTTTCTCAATGCTCACGCTGTAGGTATCTCAGTTCGGTGTAGGTCGTTCGCTCCAAGCTGG
GCTGTGTGCACGAACCCCCCGTTCAGCCCGACCGCTGCGCCTTATCCGGTAACTATCGTCTTGA
GTCCAACCCGGTAAGACACGACTTATCGCCACTGGCAGCAGCCACTGGTAACAGGATTAGCAGA
GCGAGGTATGTAGGCGGTGCTACAGAGTTCTTGAAGTGGTGGCCTAACTACGGCTACACTAGAA
GGACAGTATTTGGTATCTGCGCTCTGCTGAAGCCAGTTACCTTCGGAAAAAGAGTTGGTAGCTC
TTGATCCGGCAAACAAACCACCGCTGGTAGCGGTGGTTTTTTTGTTTGCAAGCAGCAGATTACG
CGCAGAAAAAAAGGATCTCAAGAAGATCCTTTGATCTTTTCTACGGGTCTGACGCTCAGTGGA
ACGAAAACTCACGTTAAGGGATTTTGGTCATGAGATTATCAAAAAGGATCTTCACCTAGATCCT
TTTAAATTAAAAATGAAGTTTTAAATCAATCTAAAGTATATATGAGTAAACTTGGTCTGACAGT
TACCAATGCTTAATCAGTGAGGCACCTATCTCAGCGATCTGTCTATTTCGTTCATCCATAGTTG
CCTGATCCCCGTCGTGTAGATAACTACGATACGGGAGGGCTTACCATCTGGCCCCAGTGCTGCA
ATGATACCGCGAGACCCACGCTCACCGGCTCCAGATTTATCAGCAATAAACCAGCCAGCCGGAA
GGGCCGAGCGCAGAAGTGGTCCTGCAACTTTATCCGCCTCCATCCAGTCTATTAATTGTTGCCG
GGAAGCTAGAGTAAGTAGTTCGCCAGTTAATAGTTTGCGCAACGTTGTTGCCATTGCTACAGGC
ATCGTGGTGTCACGCTCGTCGTTTGGTATGGCTTCATTCAGCTCCGGTTCCCAACGATCAAGGC
GAGTTACATGATCCCCCATGTTGTGCAAAAAAGCGGTTAGCTCCTTCGGTCCTCCGATCGTTGT
CAGAAGTAAGTTGGCCGCAGTGTTATCACTCATGGTTATGGCAGCACTGCATAATTCTCTTACT
GTCATGCCATCCGTAAGATGCTTTTCTGTGACTGGTGAGTACTCAACCAAGTCATTCTGAGAAT
AGTGTATGCGGCGACCGAGTTGCTCTTGCCCGGCGTCAATACGGGATAATACCGCGCCACATAG
CAGAACTTTAAAAGTGCTCATCATTGGAAAACGTTCTTCGGGGCGAAAACTCTCAAGGATCTTA
CCGCTGTTGAGATCCAGTTCGATGTAACCCACTCGTGCACCCAACTGATCTTCAGCATCTTTTA
CTTTCACCAGCGTTTCTGGGTGAGCAAAAACAGGAAGGCAAAATGCCGCAAAAAAGGGAATAAG
GGCGACACGGAAATGTTGAATACTCATACTCTTCCTTTTTCAATATTATTGAAGCATTTATCAG
GGTTATTGTCTCATGAGCGGATACATATTTGAATGTATTTAGAAAAATAAACAAATAGGGGTTC
CGCGCACATTTCCCCGAAAAGTGCCACCTGACGTCTAAGAAACCATTATTATCATGACATTAAC
CTATAAAAATAGGCGTATCACGAGGCCCTTTCGTC
```

FIG.10B

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 42 base pairs
        ( B ) TYPE: nucleic acid
        ( C ) STRANDEDNESS: both
        ( D ) TOPOLOGY: both ( x i ) SEQUENCE DESCRIPTION: SEQ ID NO:1:

TCGAGTTTAC CACTCCCTAT CAGTGATAGA GAAAAGTGAA AG    42

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( D ) TOPOLOGY: both ( x i ) SEQUENCE DESCRIPTION: SEQ ID NO:2:

Ser Gly Ser Ala Tyr Ser
    1                  5

( 2 ) INFORMATION FOR SEQ ID NO:3:

( i ) SEQUENCE CHARACTERISTICS:
        ( A ) LENGTH: 10 amino acids
        ( B ) TYPE: amino acid
        ( D ) TOPOLOGY: both ( x i ) SEQUENCE DESCRIPTION: SEQ ID NO:3:

Ser Gly Ser Asp Pro Ser Ile His Thr Arg
1               5                   10

( 2 ) INFORMATION FOR SEQ ID NO:4:

( i ) SEQUENCE CHARACTERISTICS:
        ( A ) LENGTH: 4 amino acids
        ( B ) TYPE: amino acid
        ( D ) TOPOLOGY: both ( x i ) SEQUENCE DESCRIPTION: SEQ ID NO:4:

Tyr Gly Gly Phe
1

( 2 ) INFORMATION FOR SEQ ID NO:5:

( i ) SEQUENCE CHARACTERISTICS:
        ( A ) LENGTH: 19 base pairs
        ( B ) TYPE: nucleic acid
        ( C ) STRANDEDNESS: both
        ( D ) TOPOLOGY: both ( x i ) SEQUENCE DESCRIPTION: SEQ ID NO:5:

TCCCTATCAG TGATAGAGA                                        19

( 2 ) INFORMATION FOR SEQ ID NO:6:

( i ) SEQUENCE CHARACTERISTICS:
        ( A ) LENGTH: 12 base pairs
        ( B ) TYPE: nucleic acid
        ( C ) STRANDEDNESS: both
        ( D ) TOPOLOGY: both ( x i ) SEQUENCE DESCRIPTION: SEQ ID NO:6:

AGGCCTATAT AA                                              12

( 2 ) INFORMATION FOR SEQ ID NO:7:

( i ) SEQUENCE CHARACTERISTICS:
        ( A ) LENGTH: 19 base pairs
        ( B ) TYPE: nucleic acid
        ( C ) STRANDEDNESS: both
        ( D ) TOPOLOGY: both ( x i ) SEQUENCE DESCRIPTION: SEQ ID NO:7:

TCTCTATCAC TGATAGGGA                                        19

( 2 ) INFORMATION FOR SEQ ID NO:8:

( i ) SEQUENCE CHARACTERISTICS:
        ( A ) LENGTH: 1008 base pairs
        ( B ) TYPE: nucleic acid
        ( C ) STRANDEDNESS: both
        ( D ) TOPOLOGY: both ( i x ) FEATURE:
        ( A ) NAME/KEY: CDS
        ( B ) LOCATION: 1..1005

( x i ) SEQUENCE DESCRIPTION: SEQ ID NO:8:

ATG TCT AGA TTA GAT AAA AGT AAA GTG ATT AAC AGC GCA TTA GAG CTG    48
Met Ser Arg Leu Asp Lys Ser Lys Val Ile Asn Ser Ala Leu Glu Leu
1               5                   10                  15

CTT AAT GAG GTC GGA ATC GAA GGT TTA ACA ACC CGT AAA CTC GCC CAG    96
Leu Asn Glu Val Gly Ile Glu Gly Leu Thr Thr Arg Lys Leu Ala Gln
            20                  25                  30

| | | | | | | | | | | | | | | | | |
|---|---|---|---|---|---|---|---|---|---|---|---|---|---|---|---|---|
| AAG | CTA | GGT | GTA | GAG | CAG | CCT | ACA | TTG | TAT | TGG | CAT | GTA | AAA | AAT | AAG | 144 |
| Lys | Leu | Gly 35 | Val | Glu | Gln | Pro | Thr 40 | Leu | Tyr | Trp | His | Val 45 | Lys | Asn | Lys | |
| CGG | GCT | TTG | CTC | GAC | GCC | TTA | GCC | ATT | GAG | ATG | TTA | GAT | AGG | CAC | CAT | 192 |
| Arg | Ala 50 | Leu | Leu | Asp | Ala | Leu 55 | Ala | Ile | Glu | Met | Leu 60 | Asp | Arg | His | His | |
| ACT | CAC | TTT | TGC | CCT | TTA | GAA | GGG | GAA | AGC | TGG | CAA | GAT | TTT | TTA | CGT | 240 |
| Thr 65 | His | Phe | Cys | Pro | Leu 70 | Glu | Gly | Glu | Ser | Trp 75 | Gln | Asp | Phe | Leu | Arg 80 | |
| AAT | AAG | GCT | AAA | AGT | TTT | AGA | TGT | GCT | TTA | CTA | AGT | CAT | CGC | GAT | GGA | 288 |
| Asn | Lys | Ala | Lys | Ser 85 | Phe | Arg | Cys | Ala | Leu 90 | Leu | Ser | His | Arg | Asp 95 | Gly | |
| GCA | AAA | GTA | CAT | TTA | GGT | ACA | CGG | CCT | ACA | GAA | AAA | CAG | TAT | GAA | ACT | 336 |
| Ala | Lys | Val | His | Leu 100 | Gly | Thr | Arg | Pro 105 | Thr | Glu | Lys | Gln | Tyr 110 | Glu | Thr | |
| CTC | GAA | AAT | CAA | TTA | GCC | TTT | TTA | TGC | CAA | CAA | GGT | TTT | TCA | CTA | GAG | 384 |
| Leu | Glu | Asn 115 | Gln | Leu | Ala | Phe | Leu 120 | Cys | Gln | Gln | Gly | Phe 125 | Ser | Leu | Glu | |
| AAT | GCA | TTA | TAT | GCA | CTC | AGC | GCT | GTG | GGG | CAT | TTT | ACT | TTA | GGT | TGC | 432 |
| Asn | Ala 130 | Leu | Tyr | Ala | Leu | Ser 135 | Ala | Val | Gly | His | Phe 140 | Thr | Leu | Gly | Cys | |
| GTA | TTG | GAA | GAT | CAA | GAG | CAT | CAA | GTC | GCT | AAA | GAA | GAA | AGG | GAA | ACA | 480 |
| Val 145 | Leu | Glu | Asp | Gln | Glu 150 | His | Gln | Val | Ala | Lys 155 | Glu | Glu | Arg | Glu | Thr 160 | |
| CCT | ACT | ACT | GAT | AGT | ATG | CCG | CCA | TTA | TTA | CGA | CAA | GCT | ATC | GAA | TTA | 528 |
| Pro | Thr | Thr | Asp | Ser 165 | Met | Pro | Pro | Leu | Leu 170 | Arg | Gln | Ala | Ile | Glu 175 | Leu | |
| TTT | GAT | CAC | CAA | GGT | GCA | GAG | CCA | GCC | TTC | TTA | TTC | GGC | CTT | GAA | TTG | 576 |
| Phe | Asp | His | Gln 180 | Gly | Ala | Glu | Pro | Ala 185 | Phe | Leu | Phe | Gly | Leu 190 | Glu | Leu | |
| ATC | ATA | TGC | GGA | TTA | GAA | AAA | CAA | CTT | AAA | TGT | GAA | AGT | GGG | TCC | GCG | 624 |
| Ile | Ile | Cys 195 | Gly | Leu | Glu | Lys | Gln 200 | Leu | Lys | Cys | Glu | Ser 205 | Gly | Ser | Ala | |
| TAC | AGC | CGC | GCG | CGT | ACG | AAA | AAC | AAT | TAC | GGG | TCT | ACC | ATC | GAG | GGC | 672 |
| Tyr | Ser | Arg 210 | Ala | Arg | Thr | Lys | Asn 215 | Asn | Tyr | Gly | Ser | Thr 220 | Ile | Glu | Gly | |
| CTG | CTC | GAT | CTC | CCG | GAC | GAC | GAC | GCC | CCC | GAA | GAG | GCG | GGG | CTG | GCG | 720 |
| Leu 225 | Leu | Asp | Leu | Pro | Asp 230 | Asp | Asp | Ala | Pro | Glu 235 | Glu | Ala | Gly | Leu | Ala 240 | |
| GCT | CCG | CGC | CTG | TCC | TTT | CTC | CCC | GCG | GGA | CAC | ACG | CGC | AGA | CTG | TCG | 768 |
| Ala | Pro | Arg | Leu | Ser 245 | Phe | Leu | Pro | Ala | Gly 250 | His | Thr | Arg | Arg | Leu 255 | Ser | |
| ACG | GCC | CCC | CCG | ACC | GAT | GTC | AGC | CTG | GGG | GAC | GAG | CTC | CAC | TTA | GAC | 816 |
| Thr | Ala | Pro | Pro 260 | Thr | Asp | Val | Ser | Leu 265 | Gly | Asp | Glu | Leu | His 270 | Leu | Asp | |
| GGC | GAG | GAC | GTG | GCG | ATG | GCG | CAT | GCC | GAC | GCG | CTA | GAC | GAT | TTC | GAT | 864 |
| Gly | Glu | Asp 275 | Val | Ala | Met | Ala | His 280 | Ala | Asp | Ala | Leu | Asp 285 | Asp | Phe | Asp | |
| CTG | GAC | ATG | TTG | GGG | GAC | GGG | GAT | TCC | CCG | GGT | CCG | GGA | TTT | ACC | CCC | 912 |
| Leu | Asp | Met 290 | Leu | Gly | Asp | Gly | Asp 295 | Ser | Pro | Gly | Pro | Gly 300 | Phe | Thr | Pro | |
| CAC | GAC | TCC | GCC | CCC | TAC | GGC | GCT | CTG | GAT | ATG | GCC | GAC | TTC | GAG | TTT | 960 |
| His | Asp | Ser | Ala | Pro 310 | Tyr | Gly | Ala | Leu | Asp 315 | Met | Ala | Asp | Phe | Glu 320 | Phe | |
| GAG | CAG | ATG | TTT | ACC | GAT | CCC | CTT | GGA | ATT | GAC | GAG | TAC | GGT | GGG | TAG | 1008 |
| Glu | Gln | Met | Phe | Thr 325 | Asp | Pro | Leu | Gly | Ile 330 | Asp | Glu | Tyr | Gly | Gly 335 | | |

(Row at 305: His Asp Ser Ala Pro Tyr Gly Ala Leu Asp Met Ala Asp Phe Glu Phe — with 305 under His)

( 2 ) INFORMATION FOR SEQ ID NO:9:

( i ) SEQUENCE CHARACTERISTICS:
    ( A ) LENGTH: 335 amino acids
    ( B ) TYPE: amino acid
    ( D ) TOPOLOGY: linear ( i i ) MOLECULE TYPE: protein ( x i ) SEQUENCE DESCRIPTION: SEQ ID NO:9:

```
Met Ser Arg Leu Asp Lys Ser Lys Val Ile Asn Ser Ala Leu Glu Leu
 1               5                  10                  15

Leu Asn Glu Val Gly Ile Glu Gly Leu Thr Thr Arg Lys Leu Ala Gln
                20                  25                  30

Lys Leu Gly Val Glu Gln Pro Thr Leu Tyr Trp His Val Lys Asn Lys
                35                  40                  45

Arg Ala Leu Leu Asp Ala Leu Ala Ile Glu Met Leu Asp Arg His His
            50                  55                  60

Thr His Phe Cys Pro Leu Glu Gly Glu Ser Trp Gln Asp Phe Leu Arg
65                      70                  75                  80

Asn Lys Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
                100                 105                 110

Leu Glu Asn Gln Leu Ala Phe Leu Cys Gln Gln Gly Phe Ser Leu Glu
            115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                     150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser Ala
        195                 200                 205

Tyr Ser Arg Ala Arg Thr Lys Asn Asn Tyr Gly Ser Thr Ile Glu Gly
    210                 215                 220

Leu Leu Asp Leu Pro Asp Asp Ala Pro Glu Glu Ala Gly Leu Ala
225                 230                 235                 240

Ala Pro Arg Leu Ser Phe Leu Pro Ala Gly His Thr Arg Arg Leu Ser
                245                 250                 255

Thr Ala Pro Pro Thr Asp Val Ser Leu Gly Asp Glu Leu His Leu Asp
            260                 265                 270

Gly Glu Asp Val Ala Met Ala His Ala Asp Ala Leu Asp Asp Phe Asp
            275                 280                 285

Leu Asp Met Leu Gly Asp Gly Asp Ser Pro Gly Pro Gly Phe Thr Pro
    290                 295                 300

His Asp Ser Ala Pro Tyr Gly Ala Leu Asp Met Ala Asp Phe Glu Phe
305                     310                 315                 320

Glu Gln Met Phe Thr Asp Pro Leu Gly Ile Asp Glu Tyr Gly Gly
                325                 330                 335
```

( 2 ) INFORMATION FOR SEQ ID NO:10:

( i ) SEQUENCE CHARACTERISTICS:
        ( A ) LENGTH: 894 base pairs
        ( B ) TYPE: nucleic acid
        ( C ) STRANDEDNESS: both (D) TOPOLOGY: both (ix) FEATURE:
  (A) NAME/KEY: CDS
  (B) LOCATION: 1..891

(xi) SEQUENCE DESCRIPTION: SEQ ID NO:10:

| | | | | | | | | | | | | | | | | |
|---|---|---|---|---|---|---|---|---|---|---|---|---|---|---|---|---|
| ATG | TCT | AGA | TTA | GAT | AAA | AGT | AAA | GTG | ATT | AAC | AGC | GCA | TTA | GAG | CTG | 48 |
| Met | Ser | Arg | Leu | Asp | Lys | Ser | Lys | Val | Ile | Asn | Ser | Ala | Leu | Glu | Leu | |
| 1 | | | | 5 | | | | 10 | | | | | | 15 | | |
| CTT | AAT | GAG | GTC | GGA | ATC | GAA | GGT | TTA | ACA | ACC | CGT | AAA | CTC | GCC | CAG | 96 |
| Leu | Asn | Glu | Val | Gly | Ile | Glu | Gly | Leu | Thr | Thr | Arg | Lys | Leu | Ala | Gln | |
| | | | 20 | | | | | 25 | | | | | 30 | | | |
| AAG | CTA | GGT | GTA | GAG | CAG | CCT | ACA | TTG | TAT | TGG | CAT | GTA | AAA | AAT | AAG | 144 |
| Lys | Leu | Gly | Val | Glu | Gln | Pro | Thr | Leu | Tyr | Trp | His | Val | Lys | Asn | Lys | |
| | | 35 | | | | | 40 | | | | | 45 | | | | |
| CGG | GCT | TTG | CTC | GAC | GCC | TTA | GCC | ATT | GAG | ATG | TTA | GAT | AGG | CAC | CAT | 192 |
| Arg | Ala | Leu | Leu | Asp | Ala | Leu | Ala | Ile | Glu | Met | Leu | Asp | Arg | His | His | |
| | 50 | | | | | 55 | | | | | 60 | | | | | |
| ACT | CAC | TTT | TGC | CCT | TTA | GAA | GGG | GAA | AGC | TGG | CAA | GAT | TTT | TTA | CGT | 240 |
| Thr | His | Phe | Cys | Pro | Leu | Glu | Gly | Glu | Ser | Trp | Gln | Asp | Phe | Leu | Arg | |
| 65 | | | | | 70 | | | | | 75 | | | | | 80 | |
| AAT | AAC | GCT | AAA | AGT | TTT | AGA | TGT | GCT | TTA | CTA | AGT | CAT | CGC | GAT | GGA | 288 |
| Asn | Asn | Ala | Lys | Ser | Phe | Arg | Cys | Ala | Leu | Leu | Ser | His | Arg | Asp | Gly | |
| | | | | 85 | | | | | 90 | | | | | 95 | | |
| GCA | AAA | GTA | CAT | TTA | GGT | ACA | CGG | CCT | ACA | GAA | AAA | CAG | TAT | GAA | ACT | 336 |
| Ala | Lys | Val | His | Leu | Gly | Thr | Arg | Pro | Thr | Glu | Lys | Gln | Tyr | Glu | Thr | |
| | | | 100 | | | | | 105 | | | | | 110 | | | |
| CTC | GAA | AAT | CAA | TTA | GCC | TTT | TTA | TGC | CAA | CAA | GGT | TTT | TCA | CTA | GAG | 384 |
| Leu | Glu | Asn | Gln | Leu | Ala | Phe | Leu | Cys | Gln | Gln | Gly | Phe | Ser | Leu | Glu | |
| | | 115 | | | | | 120 | | | | | 125 | | | | |
| AAT | GCA | TTA | TAT | GCA | CTC | AGC | GCT | GTG | GGG | CAT | TTT | ACT | TTA | GGT | TGC | 432 |
| Asn | Ala | Leu | Tyr | Ala | Leu | Ser | Ala | Val | Gly | His | Phe | Thr | Leu | Gly | Cys | |
| | 130 | | | | | 135 | | | | | 140 | | | | | |
| GTA | TTG | GAA | GAT | CAA | GAG | CAT | CAA | GTC | GCT | AAA | GAA | GAA | AGG | GAA | ACA | 480 |
| Val | Leu | Glu | Asp | Gln | Glu | His | Gln | Val | Ala | Lys | Glu | Glu | Arg | Glu | Thr | |
| 145 | | | | | 150 | | | | | 155 | | | | | 160 | |
| CCT | ACT | ACT | GAT | AGT | ATG | CCG | CCA | TTA | TTA | CGA | CAA | GCT | ATC | GAA | TTA | 528 |
| Pro | Thr | Thr | Asp | Ser | Met | Pro | Pro | Leu | Leu | Arg | Gln | Ala | Ile | Glu | Leu | |
| | | | | 165 | | | | | 170 | | | | | 175 | | |
| TTT | GAT | CAC | CAA | GGT | GCA | GAG | CCA | GCC | TTC | TTA | TTC | GGC | CTT | GAA | TTG | 576 |
| Phe | Asp | His | Gln | Gly | Ala | Glu | Pro | Ala | Phe | Leu | Phe | Gly | Leu | Glu | Leu | |
| | | | 180 | | | | | 185 | | | | | 190 | | | |
| ATC | ATA | TGC | GGA | TTA | GAA | AAA | CAA | CTT | AAA | TGT | GAA | AGT | GGG | TCT | GAT | 624 |
| Ile | Ile | Cys | Gly | Leu | Glu | Lys | Gln | Leu | Lys | Cys | Glu | Ser | Gly | Ser | Asp | |
| | | 195 | | | | | 200 | | | | | 205 | | | | |
| CCA | TCG | ATA | CAC | ACG | CGC | AGA | CTG | TCG | ACG | GCC | CCG | ACC | GAT | GTC | | 672 |
| Pro | Ser | Ile | His | Thr | Arg | Arg | Leu | Ser | Thr | Ala | Pro | Pro | Thr | Asp | Val | |
| | 210 | | | | | 215 | | | | | 220 | | | | | |
| AGC | CTG | GGG | GAC | GAG | CTC | CAC | TTA | GAC | GGC | GAG | GAC | GTG | GCG | ATG | GCG | 720 |
| Ser | Leu | Gly | Asp | Glu | Leu | His | Leu | Asp | Gly | Glu | Asp | Val | Ala | Met | Ala | |
| 225 | | | | | 230 | | | | | 235 | | | | | 240 | |
| CAT | GCC | GAC | GCG | CTA | GAC | GAT | TTC | GAT | CTG | GAC | ATG | TTG | GGG | GAC | GGG | 768 |
| His | Ala | Asp | Ala | Leu | Asp | Asp | Phe | Asp | Leu | Asp | Met | Leu | Gly | Asp | Gly | |
| | | | | 245 | | | | | 250 | | | | | 255 | | |
| GAT | TCC | CCG | GGT | CCG | GGA | TTT | ACC | CCC | CAC | GAC | TCC | GCC | CCC | TAC | GGC | 816 |
| Asp | Ser | Pro | Gly | Pro | Gly | Phe | Thr | Pro | His | Asp | Ser | Ala | Pro | Tyr | Gly | |
| | | | 260 | | | | | 265 | | | | | 270 | | | |
| GCT | CTG | GAT | ATG | GCC | GAC | TTC | GAG | TTT | GAG | CAG | ATG | TTT | ACC | GAT | GCC | 864 |
| Ala | Leu | Asp | Met | Ala | Asp | Phe | Glu | Phe | Glu | Gln | Met | Phe | Thr | Asp | Ala | |
| | | 275 | | | | | 280 | | | | | 285 | | | | |

```
CTT  GGA  ATT  GAC  GAG  TAC  GGT  GGG  TTC  TAG                                          894
Leu  Gly  Ile  Asp  Glu  Tyr  Gly  Gly  Phe
290                           295
```

( 2 ) INFORMATION FOR SEQ ID NO:11:

( i ) SEQUENCE CHARACTERISTICS:
        ( A ) LENGTH: 297 amino acids
        ( B ) TYPE: amino acid
        ( D ) TOPOLOGY: linear ( i i ) MOLECULE TYPE: protein ( x i ) SEQUENCE DESCRIPTION: SEQ ID NO:11:

```
Met  Ser  Arg  Leu  Asp  Lys  Ser  Lys  Val  Ile  Asn  Ser  Ala  Leu  Glu  Leu
1                     5                    10                            15

Leu  Asn  Glu  Val  Gly  Ile  Glu  Gly  Leu  Thr  Thr  Arg  Lys  Leu  Ala  Gln
                20                   25                      30

Lys  Leu  Gly  Val  Glu  Gln  Pro  Thr  Leu  Tyr  Trp  His  Val  Lys  Asn  Lys
           35                        40                       45

Arg  Ala  Leu  Leu  Asp  Ala  Leu  Ala  Ile  Glu  Met  Leu  Asp  Arg  His  His
     50                        55                       60

Thr  His  Phe  Cys  Pro  Leu  Glu  Gly  Glu  Ser  Trp  Gln  Asp  Phe  Leu  Arg
65                       70                   75                            80

Asn  Asn  Ala  Lys  Ser  Phe  Arg  Cys  Ala  Leu  Leu  Ser  His  Arg  Asp  Gly
                85                        90                       95

Ala  Lys  Val  His  Leu  Gly  Thr  Arg  Pro  Thr  Glu  Lys  Gln  Tyr  Glu  Thr
               100                       105                      110

Leu  Glu  Asn  Gln  Leu  Ala  Phe  Leu  Cys  Gln  Gln  Gly  Phe  Ser  Leu  Glu
               115                       120                      125

Asn  Ala  Leu  Tyr  Ala  Leu  Ser  Ala  Val  Gly  His  Phe  Thr  Leu  Gly  Cys
     130                       135                      140

Val  Leu  Glu  Asp  Gln  Glu  His  Gln  Val  Ala  Lys  Glu  Glu  Arg  Glu  Thr
145                      150                      155                      160

Pro  Thr  Thr  Asp  Ser  Met  Pro  Pro  Leu  Leu  Arg  Gln  Ala  Ile  Glu  Leu
                    165                       170                      175

Phe  Asp  His  Gln  Gly  Ala  Glu  Pro  Ala  Phe  Leu  Phe  Gly  Leu  Glu  Leu
               180                       185                      190

Ile  Ile  Cys  Gly  Leu  Glu  Lys  Gln  Leu  Lys  Cys  Glu  Ser  Gly  Ser  Asp
          195                       200                      205

Pro  Ser  Ile  His  Thr  Arg  Arg  Leu  Ser  Thr  Ala  Pro  Pro  Thr  Asp  Val
     210                       215                      220

Ser  Leu  Gly  Asp  Glu  Leu  His  Leu  Asp  Gly  Glu  Asp  Val  Ala  Met  Ala
225                      230                      235                      240

His  Ala  Asp  Ala  Leu  Asp  Asp  Phe  Asp  Leu  Asp  Met  Leu  Gly  Asp  Gly
               245                       250                      255

Asp  Ser  Pro  Gly  Pro  Gly  Phe  Thr  Pro  His  Asp  Ser  Ala  Pro  Tyr  Gly
               260                       265                      270

Ala  Leu  Asp  Met  Ala  Asp  Phe  Glu  Phe  Glu  Gln  Met  Phe  Thr  Asp  Ala
               275                       280                      285

Leu  Gly  Ile  Asp  Glu  Tyr  Gly  Gly  Phe
290                       295
```

( 2 ) INFORMATION FOR SEQ ID NO:12:

( i ) SEQUENCE CHARACTERISTICS:
        ( A ) LENGTH: 450 base pairs ( B ) TYPE: nucleic acid
( C ) STRANDEDNESS: both
( D ) TOPOLOGY: both ( x i ) SEQUENCE DESCRIPTION: SEQ ID NO:12:

| | | | | | | |
|---|---|---|---|---|---|---|
| GAATTCCTCG | AGTTTACCAC | TCCCTATCAG | TGATAGAGAA | AAGTGAAAGT | CGAGTTTACC | 60 |
| ACTCCCTATC | AGTGATAGAG | AAAAGTGAAA | GTCGAGTTTA | CCACTCCCTA | TCAGTGATAG | 120 |
| AGAAAAGTGA | AAGTCGAGTT | TACCACTCCC | TATCAGTGAT | AGAGAAAAGT | GAAAGTCGAG | 180 |
| TTTACCACTC | CCTATCAGTG | ATAGAGAAAA | GTGAAAGTCG | AGTTTACCAC | TCCCTATCAG | 240 |
| TGATAGAGAA | AAGTGAAAGT | CGAGTTTACC | ACTCCCTATC | AGTGATAGAG | AAAAGTGAAA | 300 |
| GTCGAGCTCG | GTACCCGGGT | CGAGTAGGCG | TGTACGGTGG | GAGGCCTATA | TAAGCAGAGC | 360 |
| TCGTTTAGTG | AACCGTCAGA | TCGCCTGGAG | ACGCCATCCA | CGCTGTTTTG | ACCTCCATAG | 420 |
| AAGACACCGG | GACCGATCCA | GCCTCCGCGG | | | | 450 |

( 2 ) INFORMATION FOR SEQ ID NO:13:

( i ) SEQUENCE CHARACTERISTICS:
( A ) LENGTH: 450 base pairs
( B ) TYPE: nucleic acid
( C ) STRANDEDNESS: both
( D ) TOPOLOGY: linear ( x i ) SEQUENCE DESCRIPTION: SEQ ID NO:13:

| | | | | | | |
|---|---|---|---|---|---|---|
| GAATTCCTCG | ACCCGGGTAC | CGAGCTCGAC | TTTCACTTTT | CTCTATCACT | GATAGGGAGT | 60 |
| GGTAAACTCG | ACTTTCACTT | TTCTCTATCA | CTGATAGGGA | GTGGTAAACT | CGACTTTCAC | 120 |
| TTTTCTCTAT | CACTGATAGG | GAGTGGTAAA | CTCGACTTTC | ACTTTTCTCT | ATCACTGATA | 180 |
| GGGAGTGGTA | AACTCGACTT | TCACTTTTCT | CTATCACTGA | TAGGGAGTGG | TAAACTCGAC | 240 |
| TTTCACTTTT | CTCTATCACT | GATAGGGAGT | GGTAAACTCG | ACTTTCACTT | TTCTCTATCA | 300 |
| CTGATAGGGA | GTGGTAAACT | CGAGTAGGCG | TGTACGGTGG | GAGGCCTATA | TAAGCAGAGC | 360 |
| TCGTTTAGTG | AACCGTCAGA | TCGCCTGGAG | ACGCCATCCA | CGCTGTTTTG | ACCTCCATAG | 420 |
| AAGACACCGG | GACCGATCCA | GCCTCCGCGG | | | | 450 |

( 2 ) INFORMATION FOR SEQ ID NO:14:

( i ) SEQUENCE CHARACTERISTICS:
( A ) LENGTH: 398 base pairs
( B ) TYPE: nucleic acid
( C ) STRANDEDNESS: both
( D ) TOPOLOGY: both ( x i ) SEQUENCE DESCRIPTION: SEQ ID NO:14:

| | | | | | | |
|---|---|---|---|---|---|---|
| GAGCTCGACT | TTCACTTTTC | TCTATCACTG | ATAGGGAGTG | GTAAACTCGA | CTTTCACTTT | 60 |
| TCTCTATCAC | TGATAGGGAG | TGGTAAACTC | GACTTTCACT | TTTCTCTATC | ACTGATAGGG | 120 |
| AGTGGTAAAC | TCGACTTTCA | CTTTTCTCTA | TCACTGATAG | GGAGTGGTAA | ACTCGACTTT | 180 |
| CACTTTTCTC | TATCACTGAT | AGGGAGTGGT | AAACTCGACT | TTCACTTTTC | TCTATCACTG | 240 |
| ATAGGGAGTG | GTAAACTCGA | CTTTCACTTT | TCTCTATCAC | TGATAGGGAG | TGGTAAACTC | 300 |
| GAGATCCGGC | GAATTCGAAC | ACGCAGATGC | AGTCGGGGCG | GCGCGGTCCG | AGGTCCACTT | 360 |
| CGCATATTAA | GGTGACGCGT | GTGGCCTCGA | ACACCGAG | | | 398 |

( 2 ) INFORMATION FOR SEQ ID NO:15:

( i ) SEQUENCE CHARACTERISTICS:
( A ) LENGTH: 6244 base pairs ( B ) TYPE: nucleic acid
( C ) STRANDEDNESS: both
( D ) TOPOLOGY: both ( x i ) SEQUENCE DESCRIPTION: SEQ ID NO:15:

```
CTCGAGTTTA CCACTCCCTA TCAGTGATAG AGAAAAGTGA AAGTCGAGTT TACCACTCCC      60
TATCAGTGAT AGAGAAAAGT GAAAGTCGAG TTTACCACTC CCTATCAGTG ATAGAGAAAA     120
GTGAAAGTCG AGTTTACCAC TCCCTATCAG TGATAGAGAA AAGTGAAAGT CGAGTTTACC     180
ACTCCCTATC AGTGATAGAG AAAAGTGAAA GTCGAGTTTA CCACTCCCTA TCAGTGATAG     240
AGAAAAGTGA AAGTCGAGTT TACCACTCCC TATCAGTGAT AGAGAAAAGT GAAAGTCGAG     300
CTCGGTACCC GGGTCGAGTA GGCGTGTACG GTGGGAGGCC TATATAAGCA GAGCTCGTTT     360
AGTGAACCGT CAGATCGCCT GGAGACGCCA TCCACGCTGT TTTGACCTCC ATAGAAGACA     420
CCGGGACCGA TCCAGCCTCC GCGGCCCCGA ATTCGAGCTC GGTACCGGGC CCCCCCTCGA     480
GGTCGACGGT ATCGATAAGC TTGATATCGA ATTCAGGAG GTGGAGATCC GCGGGTCCAG      540
CCAAACCCCA CACCCATTTT CTCCTCCCTC TGCCCCTATA TCCCGGCACC CCTCCTCCT     600
AGCCCTTTCC CTCCTCCCGA GAGACGGGGG AGGAGAAAAG GGAGTTCAG GTCGACATGA      660
CTGAGCTGAA GGCAAAGGAA CCTCGGGCTC CCACGTGGC GGGCGGCGCG CCCTCCCCCA      720
CCGAGGTCGG ATCCCAGCTC CTGGGTCGCC CGGACCCTGG CCCCTTCCAG GGGAGCCAGA     780
CCTCAGAGGC CTCGTCTGTA GTCTCCGCCA TCCCCATCTC CCTGGACGGG TTGCTCTTCC     840
CCCGGCCCTG TCAGGGGCAG AACCCCCCAG ACGGGAAGAC GCAGGACCCA CCGTCGTTGT     900
CAGACGTGGA GGGCGCATTT CCTGGAGTCG AAGCCCCGGA GGGGGCAGGA GACAGCAGCT     960
CGAGACCTCC AGAAAAGGAC AGCGGCCTGC TGGACAGTGT CCTCGACACG CTCCTGGCGC    1020
CCTCGGGTCC CGGGCAGAGC CACGCCAGCC CTGCCACCTG CGAGGCCATC AGCCCGTGGT    1080
GCCTGTTTGG CCCCGACCTT CCCGAAGACC CCCGGGCTGC CCCCGCTACC AAAGGGGTGT    1140
TGGCCCCGCT CATGAGCCGA CCCGAGGACA AGGCAGGCGA CAGCTCTGGG ACGGCAGCGG    1200
CCCACAAGGT GCTGCCCAGG GGACTGTCAC CATCCAGGCA GCTGCTGCTC CCCTCCTCTG    1260
GGAGCCCTCA CTGGCCGGCA GTGAAGCCAT CCCCGCAGCC CGCTGCGGTG CAGGTAGACG    1320
AGGAGGACAG CTCCGAATCC GAGGGCACCG TGGGCCCGCT CCTGAAGGGC AACCTCGGG     1380
CACTGGGAGG CACGGCGGCC GGAGGAGGAG CTGCCCCCGT CGCGTCTGGA GCGGCCGCAG    1440
GAGGCGTCGC CCTTGTCCCC AAGGAAGATT CTCGCTTCTC GGCGCCCAGG GTCTCCTTGG    1500
CGGAGCAGGA CGCGCCGGTG GCGCCTGGGC GCTCCCGCT GGCCACCTCG GTGGTGGATT     1560
TCATCCACGT GCCCATCCTG CCTCTCAACC ACGCTTTCCT GGCCACCCGC ACCAGGCAGC    1620
TGCTGGAGGG GGAGAGCTAC GACGGCGGGG CCGCGGCCGC CAGCCCCTTC GTCCCGCAGC    1680
GGGGCTCCCC CTCTGCCTCG TCCACCCCTG TGGCGGGCGG CGACTTCCCC GACTGCACCT    1740
ACCCGCCCGA CGCCGAGCCC AAAGATGACG CGTTCCCCCT CTACGGCGAC TTCCAGCCGC    1800
CCGCCCTCAA GATAAAGGAG GAGGAAGAAG CCGCCGAGGC CGCGGCGCGC TCCCGCGTA     1860
CGTACCTGGT GGCTGGTGCA AACCCGCCG CCTTCCCGGA CTTCCAGCTG GCAGCGCCGC     1920
CGCCACCCTC GCTGCCGCCT CGAGTGCCCT CGTCCAGACC CGGGAAGCG GCGGTGGCGG     1980
CCTCCCCAGG CAGTGCCTCC GTCTCCTCCT CGTCCTCGTC GGGGTCGACC CTGGAGTGCA    2040
TCCTGTACAA GGCAGAAGGC GCGCCGCCCC AGCAGGGCCC CTTCGCGCCG CTGCCCTGCA    2100
AGCCTCCGGG CGCCGGCGCC TGCCTGCTCC CGCGGGACGG CCTGCCCTCC ACCTCGCCT     2160
CGGGCGCAGC CGCCGGGGCC GCCCCTGCGC TCTACCCGAC GCTCGGCCTC AACGGACTCC    2220
```

| | | | | | |
|---|---|---|---|---|---|
| CGCAACTCGG | CTACCAGGCC | GCCGTGCTCA | AGGAGGGCCT | GCCGCAGGTC | TACACGCCCT | 2280 |
| ATCTCAACTA | CCTGAGGCCG | GATTCAGAAG | CCAGTCAGAG | CCCACAGTAC | AGCTTCGAGT | 2340 |
| CACTACCTCA | GAAGATTTGT | TTGATCTGTG | GGGATGAAGC | ATCAGGCTGT | CATTATGGTG | 2400 |
| TCCTCACCTG | TGGGAGCTGT | AAGGTCTTCT | TTAAAGGGC | AATGGAAGGG | CAGCATAACT | 2460 |
| ATTTATGTGC | TGGAAGAAAT | GACTGCATTG | TTGATAAAAT | CCGCAGGAAA | AACTGCCCGG | 2520 |
| CGTGTCGCCT | TAGAAAGTGC | TGTCAAGCTG | GCATGGTCCT | TGGAGGGCGA | AAGTTTAAAA | 2580 |
| AGTTCAATAA | AGTCAGAGTC | ATGAGAGCAC | TCGATGCTGT | TGCTCTCCCA | CAGCCAGTGG | 2640 |
| GCATTCCAAA | TGAAAGCCAA | CGAATCACTT | TTTCTCCAAG | TCAAGAGATA | CAGTTAATTC | 2700 |
| CCCCTCTAAT | CAACCTGTTA | ATGAGCATTG | AACCAGATGT | GATCTATGCA | GGACATGACA | 2760 |
| ACACAAAGCC | TGATACCTCC | AGTTCTTTGC | TGACGAGTCT | TAATCAACTA | GGCGAGCGGC | 2820 |
| AACTTCTTTC | AGTGGTAAAA | TGGTCCAAAT | CTCTTCCAGG | TTTTCGAAAC | TTACATATTG | 2880 |
| ATGACCAGAT | AACTCTCATC | CAGTATTCTT | GGATGAGTTT | AATGGTATTT | GGACTAGGAT | 2940 |
| GGAGATCCTA | CAAACATGTC | AGTGGGCAGA | TGCTGTATTT | TGCACCTGAT | CTAATATTAA | 3000 |
| ATGAACAGCG | GATGAAAGAA | TCATCATTCT | ATTCACTATG | CCTTACCATG | TGGCAGATAC | 3060 |
| CGCAGGAGTT | TGTCAAGCTT | CAAGTTAGCC | AAGAAGAGTT | CCTCTGCATG | AAAGTATTAC | 3120 |
| TACTTCTTAA | TACAATTCCT | TTGGAAGGAC | TAAGAAGTCA | AAGCCAGTTT | GAAGAGATGA | 3180 |
| GATCAAGCTA | CATTAGAGAG | CTCATCAAGG | CAATTGGTTT | GAGGCAAAAA | GGAGTTGTTT | 3240 |
| CCAGCTCACA | GCGTTTCTAT | CAGCTCACAA | AACTTCTTGA | TAACTTGCAT | GATCTTGTCA | 3300 |
| AACAACTTCA | CCTGTACTGC | CTGAATACAT | TTATCCAGTC | CCGGGCGCTG | AGTGTTGAAT | 3360 |
| TTCCAGAAAT | GATGTCTGAA | GTTATTGCTG | CACAGTTACC | CAAGATATTG | GCAGGGATGG | 3420 |
| TGAAACCACT | TCTCTTTCAT | AAAAAGTGAA | TGTCAATTAT | TTTTCAAAGA | ATTAAGTGTT | 3480 |
| GTGGTATGTC | TTTCGTTTTG | GTCAGGATTA | TGACGTCTCG | AGTTTTTATA | ATATTCTGAA | 3540 |
| AGGGAATTCC | TGCAGCCCGG | GGGATCCACT | AGTTCTAGAG | GATCCAGACA | TGATAAGATA | 3600 |
| CATTGATGAG | TTTGGACAAA | CCACAACTAG | AATGCAGTGA | AAAAAATGCT | TTATTTGTGA | 3660 |
| AATTTGTGAT | GCTATTGCTT | TATTTGTAAC | CATTATAAGC | TGCAATAAAC | AAGTTAACAA | 3720 |
| CAACAATTGC | ATTCATTTTA | TGTTTCAGGT | TCAGGGGGAG | GTGTGGGAGG | TTTTTTAAAG | 3780 |
| CAAGTAAAAC | CTCTACAAAT | GTGGTATGGC | TGATTATGAT | CCTGCAAGCC | TCGTCGTCTG | 3840 |
| GCCGGACCAC | GCTATCTGTG | CAAGGTCCCC | GGACGCGCGC | TCCATGAGCA | GAGCGCCCGC | 3900 |
| CGCCGAGGCA | AGACTCGGGC | GGCGCCCTGC | CCGTCCCACC | AGGTCAACAG | CGGTAACCG | 3960 |
| GCCTCTTCAT | CGGGAATGCG | CGCGACCTTC | AGCATCGCCG | GCATGTCCCC | TGGCGGACGG | 4020 |
| GAAGTATCAG | CTCGACCAAG | CTTGGCGAGA | TTTTCAGGAG | CTAAGGAAGC | TAAAATGGAG | 4080 |
| AAAAAAATCA | CTGGATATAC | CACCGTTGAT | ATATCCCAAT | GGCATCGTAA | AGAACATTTT | 4140 |
| GAGGCATTTC | AGTCAGTTGC | TCAATGTACC | TATAACCAGA | CCGTTCAGCT | GCATTAATGA | 4200 |
| ATCGGCCAAC | GCGCGGGGAG | AGGCGGTTTG | CGTATTGGGC | GCTCTTCCGC | TTCCTCGCTC | 4260 |
| ACTGACTCGC | TGCGCTCGGT | CGTTCGGCTG | CGGCGAGCGG | TATCAGCTCA | CTCAAAGGCG | 4320 |
| GTAATACGGT | TATCCACAGA | ATCAGGGGAT | AACGCAGGAA | AGAACATGTG | AGCAAAAGGC | 4380 |
| CAGCAAAAGG | CCAGGAACCG | TAAAAAGGCC | GCGTTGCTGG | CGTTTTTCCA | TAGGCTCCGC | 4440 |
| CCCCCTGACG | AGCATCACAA | AAATCGACGC | TCAAGTCAGA | GGTGGCGAAA | CCCGACAGGA | 4500 |
| CTATAAAGAT | ACCAGGCGTT | TCCCCCTGGA | AGCTCCCTCG | TGCGCTCTCC | TGTTCCGACC | 4560 |

| | | | | | |
|---|---|---|---|---|---|
| CTGCCGCTTA | CCGGATACCT | GTCCGCCTTT | CTCCCTTCGG | GAAGCGTGGC | GCTTTCTCAA | 4620 |
| TGCTCACGCT | GTAGGTATCT | CAGTTCGGTG | TAGGTCGTTC | GCTCCAAGCT | GGGCTGTGTG | 4680 |
| CACGAACCCC | CCGTTCAGCC | CGACCGCTGC | GCCTTATCCG | GTAACTATCG | TCTTGAGTCC | 4740 |
| AACCCGGTAA | GACACGACTT | ATCGCCACTG | GCAGCAGCCA | CTGGTAACAG | GATTAGCAGA | 4800 |
| GCGAGGTATG | TAGGCGGTGC | TACAGAGTTC | TTGAAGTGGT | GGCCTAACTA | CGGCTACACT | 4860 |
| AGAAGGACAG | TATTTGGTAT | CTGCGCTCTG | CTGAAGCCAG | TTACCTTCGG | AAAAAGAGTT | 4920 |
| GGTAGCTCTT | GATCCGGCAA | ACAAACCACC | GCTGGTAGCG | GTGGTTTTTT | TGTTTGCAAG | 4980 |
| CAGCAGATTA | CGCGCAGAAA | AAAAGGATCT | CAAGAAGATC | CTTTGATCTT | TTCTACGGGG | 5040 |
| TCTGACGCTC | AGTGGAACGA | AAACTCACGT | TAAGGGATTT | TGGTCATGAG | ATTATCAAAA | 5100 |
| AGGATCTTCA | CCTAGATCCT | TTTAAATTAA | AAATGAAGTT | TTAAATCAAT | CTAAAGTATA | 5160 |
| TATGAGTAAA | CTTGGTCTGA | CAGTTACCAA | TGCTTAATCA | GTGAGGCACC | TATCTCAGCG | 5220 |
| ATCTGTCTAT | TTCGTTCATC | CATAGTTGCC | TGACTCCCCG | TCGTGTAGAT | AACTACGATA | 5280 |
| CGGGAGGGCT | TACCATCTGG | CCCCAGTGCT | GCAATGATAC | CGCGAGACCC | ACGCTCACCG | 5340 |
| GCTCCAGATT | TATCAGCAAT | AAACCAGCCA | GCCGGAAGGG | CCGAGCGCAG | AAGTGGTCCT | 5400 |
| GCAACTTTAT | CCGCCTCCAT | CCAGTCTATT | AATTGTTGCC | GGGAAGCTAG | AGTAAGTAGT | 5460 |
| TCGCCAGTTA | ATAGTTTGCG | CAACGTTGTT | GCCATTGCTA | CAGGCATCGT | GGTGTCACGC | 5520 |
| TCGTCGTTTG | GTATGGCTTC | ATTCAGCTCC | GGTTCCCAAC | GATCAAGGCG | AGTTACATGA | 5580 |
| TCCCCCATGT | TGTGCAAAAA | AGCGGTTAGC | TCCTTCGGTC | CTCCGATCGT | TGTCAGAAGT | 5640 |
| AAGTTGGCCG | CAGTGTTATC | ACTCATGGTT | ATGGCAGCAC | TGCATAATTC | TCTTACTGTC | 5700 |
| ATGCCATCCG | TAAGATGCTT | TTCTGTGACT | GGTGAGTACT | CAACCAAGTC | ATTCTGAGAA | 5760 |
| TAGTGTATGC | GGCGACCGAG | TTGCTCTTGC | CCGGCGTCAA | TACGGGATAA | TACCGCGCCA | 5820 |
| CATAGCAGAA | CTTTAAAAGT | GCTCATCATT | GGAAAACGTT | CTTCGGGGCG | AAAACTCTCA | 5880 |
| AGGATCTTAC | CGCTGTTGAG | ATCCAGTTCG | ATGTAACCCA | CTCGTGCACC | CAACTGATCT | 5940 |
| TCAGCATCTT | TTACTTTCAC | CAGCGTTTCT | GGGTGAGCAA | AAACAGGAAG | GCAAAATGCC | 6000 |
| GCAAAAAAGG | GAATAAGGGC | GACACGGAAA | TGTTGAATAC | TCATACTCTT | CCTTTTTCAA | 6060 |
| TATTATTGAA | GCATTTATCA | GGGTTATTGT | CTCATGAGCG | GATACATATT | TGAATGTATT | 6120 |
| TAGAAAAATA | AACAAATAGG | GGTTCCGCGC | ACATTTCCCC | GAAAAGTGCC | ACCTGACGTC | 6180 |
| TAAGAAACCA | TTATTATCAT | GACATTAACC | TATAAAAATA | GGCGTATCAC | GAGGCCCTTT | 6240 |
| CGTC | | | | | | 6244 |

( 2 ) INFORMATION FOR SEQ ID NO:16:

( i ) SEQUENCE CHARACTERISTICS:
        ( A ) LENGTH: 4963 base pairs
        ( B ) TYPE: nucleic acid
        ( C ) STRANDEDNESS: both
        ( D ) TOPOLOGY: both ( x i ) SEQUENCE DESCRIPTION: SEQ ID NO:16:

| | | | | | |
|---|---|---|---|---|---|
| CTCGAGTTTA | CCACTCCCTA | TCAGTGATAG | AGAAAAGTGA | AAGTCGAGTT | TACCACTCCC | 60 |
| TATCAGTGAT | AGAGAAAAGT | GAAAGTCGAG | TTTACCACTC | CCTATCAGTG | ATAGAGAAAA | 120 |
| GTGAAAGTCG | AGTTTACCAC | TCCCTATCAG | TGATAGAGAA | AAGTGAAAGT | CGAGTTTACC | 180 |
| ACTCCCTATC | AGTGATAGAG | AAAAGTGAAA | GTCGAGTTTA | CCACTCCCTA | TCAGTGATAG | 240 |
| AGAAAAGTGA | AAGTCGAGTT | TACCACTCCC | TATCAGTGAT | AGAGAAAAGT | GAAAGTCGAG | 300 |

| | | | | | |
|---|---|---|---|---|---|
| CTCGGTACCC | GGGTCGAGTA | GGCGTGTACG | GTGGGAGGCC | TATATAAGCA | GAGCTCGTTT | 360
| AGTGAACCGT | CAGATCGCCT | GGAGACGCCA | TCCACGCTGT | TTTGACCTCC | ATAGAAGACA | 420
| CCGGGACCGA | TCCAGCCTCC | GCGGCCCCGA | ATTCCGGCCA | CGACCATGAC | CATGACCCTC | 480
| CACACCAAAG | CATCTGGGAT | GGCCCTACTG | CATCAGATCC | AAGGGAACGA | GCTGGAGCCC | 540
| CTGAACCGTC | CGCAGCTCAA | GATCCCCCTG | GAGCGGCCCC | TGGGCGAGGT | GTACCTGGAC | 600
| AGCAGCAAGC | CCGCCGTGTA | CAACTACCCC | GAGGGCGCCG | CCTACGAGTT | CAACGCCGCG | 660
| GCCGCCGCCA | ACGCGCAGGT | CTACGGTCAG | ACCGGCCTCC | CCTACGGCCC | CGGGTCTGAG | 720
| GCTGCGGCGT | TCGGCTCCAA | CGGCCTGGGG | GGTTTCCCCC | CACTCAACAG | CGTGTCTCCG | 780
| AGCCCGCTGA | TGCTACTGCA | CCCGCCGCCG | CAGCTGTCGC | CTTTCCTGCA | GCCCCACGGC | 840
| CAGCAGGTGC | CCTACTACCT | GGAGAACGAG | CCCAGCGGCT | ACACGGTGCG | CGAGGCCGGC | 900
| CCGCCGGCAT | TCTACAGGCC | AAATTCAGAT | AATCGACGCC | AGGGTGGCAG | AGAAAGATTG | 960
| GCCAGTACCA | ATGACAAGGG | AAGTATGGCT | ATGGAATCTG | CCAAGGAGAC | TCGCTACTGT | 1020
| GCAGTGTGCA | ATGACTATGC | TTCAGGCTAC | CATTATGGAG | TCTGGTCCTG | TGAGGGCTGC | 1080
| AAGGCCTTCT | TCAAGAGAAG | TATTCAAGGA | CATAACGACT | ATATGTGTCC | AGCCACCAAC | 1140
| CAGTGCACCA | TTGATAAAAA | CAGGAGGAAG | AGCTGCCAGG | CCTGCCGGCT | CCGCAAATGC | 1200
| TACGAAGTGG | GAATGATGAA | AGGTGGGATA | CGAAAAGACC | GAAGAGGAGG | GAGAATGTTG | 1260
| AAACACAAGC | GCCAGAGAGA | TGATGGGGAG | GGCAGGGGTG | AAGTGGGGTC | TGCTGGAGAC | 1320
| ATGAGAGCTG | CCAACCTTTG | GCCAAGCCCG | CTCATGATCA | AACGCTCTAA | GAAGAACAGC | 1380
| CTGGCCTTGT | CCCTGACGGC | CGACCAGATG | GTCATGGCCT | TGTTGGATGC | TGAGCCCCCC | 1440
| ATACTCTATT | CCGAGTATGA | TCCTACCAGA | CCCTTCAGTG | AAGCTTCGAT | GATGGGCTTA | 1500
| CTGACCAACC | TGGCAGACAG | GGAGCTGGTT | CACATGATCA | ACTGGGCGAA | GAGGGTGCCA | 1560
| GGCTTTGTGG | ATTTGACCCT | CCATGATCAG | GTCCACCTTC | TAGAATGTGC | CTGGCTAGAG | 1620
| ATCCTGATGA | TTGGTCTCGT | CTGGCGCTCC | ATGGAGCACC | CAGTGAAGCT | ACTGTTTGCT | 1680
| CCTAACTTGC | TCTTGGACAG | GAACCAGGGA | AAATGTGTAG | AGGGCATGGT | GGAGATCTTC | 1740
| GACATGCTGC | TGGCTACATC | ATCTCGGTTC | CGCATGATGA | ATCTGCAGGG | AGAGGAGTTT | 1800
| GTGTGCCTCA | AATCTATTAT | TTTGCTTAAT | TCTGGAGTGT | ACACATTTCT | GTCCAGCACC | 1860
| CTGAAGTCTC | TGGAAGAGAA | GGACCATATC | CACCGAGTCC | TGGACAAGAT | CACAGACACT | 1920
| TTGATCCACC | TGATGGCCAA | GGCAGGCCTG | ACCCTGCAGC | AGCAGCACCA | GCGGCTGGCC | 1980
| CAGCTCCTCC | TCATCCTCTC | CCACATCAGG | CACATGAGTA | ACAAAGGCAT | GGAGCATCTG | 2040
| TACAGCATGA | AGTGCAAGAA | CGTGGTGCCC | CTCTATGACC | TGCTGCTGGA | GATGCTGGAC | 2100
| GCCCACCGCC | TACATGCGCC | CACTAGCCGT | GGAGGGGCAT | CCGTGGAGGA | GACGGACCAA | 2160
| AGCCACTTGG | CCACTGCGGG | CTCTACTTCA | TCGCATTCCT | TGCAAAAGTA | TTACATCACG | 2220
| GGGGAGGCAG | AGGGTTTCCC | TGCCACAGTC | TGAGAGCTCC | CTGGCGGAAT | TCGAGCTCGG | 2280
| TACCCGGGGA | TCCTCTAGAG | GATCCAGACA | TGATAAGATA | CATTGATGAG | TTTGGACAAA | 2340
| CCACAACTAG | AATGCAGTGA | AAAAAATGCT | TTATTTGTGA | AATTTGTGAT | GCTATTGCTT | 2400
| TATTTGTAAC | CATTATAAGC | TGCAATAAAC | AAGTTAACAA | CAACAATTGC | ATTCATTTTA | 2460
| TGTTTCAGGT | TCAGGGGGAG | GTGTGGGAGG | TTTTTTAAAG | CAAGTAAAAC | CTCTACAAAT | 2520
| GTGGTATGGC | TGATTATGAT | CCTGCAAGCC | TCGTCGTCTG | GCCGGACCAC | GCTATCTGTG | 2580
| CAAGGTCCCC | GGACGCGCGC | TCCATGAGCA | GAGCGCCCGC | CGCCGAGGCA | AGACTCGGGC | 2640
| GGCGCCCTGC | CCGTCCCACC | AGGTCAACAG | GCGGTAACCG | GCCTCTTCAT | CGGGAATGCG | 2700

```
CGCGACCTTC AGCATCGCCG GCATGTCCCC TGGCGGACGG GAAGTATCAG CTCGACCAAG   2760
CTTGGCGAGA TTTTCAGGAG CTAAGGAAGC TAAAATGGAG AAAAAAATCA CTGGATATAC   2820
CACCGTTGAT ATATCCCAAT GGCATCGTAA AGAACATTTT GAGGCATTTC AGTCAGTTGC   2880
TCAATGTACC TATAACCAGA CCGTTCAGCT GCATTAATGA ATCGGCCAAC GCGCGGGGAG   2940
AGGCGGTTTG CGTATTGGGC GCTCTTCCGC TTCCTCGCTC ACTGACTCGC TGCGCTCGGT   3000
CGTTCGGCTG CGGCGAGCGG TATCAGCTCA CTCAAAGGCG GTAATACGGT TATCCACAGA   3060
ATCAGGGGAT AACGCAGGAA AGAACATGTG AGCAAAAGGC CAGCAAAAGG CCAGGAACCG   3120
TAAAAAGGCC GCGTTGCTGG CGTTTTTCCA TAGGCTCCGC CCCCCTGACG AGCATCACAA   3180
AAATCGACGC TCAAGTCAGA GGTGGCGAAA CCCGACAGGA CTATAAAGAT ACCAGGCGTT   3240
TCCCCCTGGA AGCTCCCTCG TGCGCTCTCC TGTTCCGACC CTGCCGCTTA CCGGATACCT   3300
GTCCGCCTTT CTCCCTTCGG GAAGCGTGGC GCTTTCTCAA TGCTCACGCT GTAGGTATCT   3360
CAGTTCGGTG TAGGTCGTTC GCTCCAAGCT GGGCTGTGTG CACGAACCCC CCGTTCAGCC   3420
CGACCGCTGC GCCTTATCCG GTAACTATCG TCTTGAGTCC AACCCGGTAA GACACGACTT   3480
ATCGCCACTG GCAGCAGCCA CTGGTAACAG GATTAGCAGA GCGAGGTATG TAGGCGGTGC   3540
TACAGAGTTC TTGAAGTGGT GGCCTAACTA CGGCTACACT AGAAGGACAG TATTTGGTAT   3600
CTGCGCTCTG CTGAAGCCAG TTACCTTCGG AAAAAGAGTT GGTAGCTCTT GATCCGGCAA   3660
ACAAACCACC GCTGGTAGCG GTGGTTTTTT TGTTTGCAAG CAGCAGATTA CGCGCAGAAA   3720
AAAAGGATCT CAAGAAGATC CTTTGATCTT TTCTACGGGG TCTGACGCTC AGTGGAACGA   3780
AAACTCACGT TAAGGGATTT TGGTCATGAG ATTATCAAAA AGGATCTTCA CCTAGATCCT   3840
TTTAAATTAA AAATGAAGTT TTAAATCAAT CTAAAGTATA TATGAGTAAA CTTGGTCTGA   3900
CAGTTACCAA TGCTTAATCA GTGAGGCACC TATCTCAGCG ATCTGTCTAT TTCGTTCATC   3960
CATAGTTGCC TGATCCCCGT CGTGTAGATA ACTACGATAC GGGAGGGCTT ACCATCTGGC   4020
CCCAGTGCTG CAATGATACC GCGAGACCCA CGCTCACCGG CTCCAGATTT ATCAGCAATA   4080
AACCAGCCAG CCGGAAGGGC CGAGCGCAGA AGTGGTCCTG CAACTTTATC CGCCTCCATC   4140
CAGTCTATTA ATTGTTGCCG GGAAGCTAGA GTAAGTAGTT CGCCAGTTAA TAGTTTGCGC   4200
AACGTTGTTG CCATTGCTAC AGGCATCGTG GTGTCACGCT CGTCGTTTGG TATGGCTTCA   4260
TTCAGCTCCG GTTCCCAACG ATCAAGGCGA GTTACATGAT CCCCCATGTT GTGCAAAAAA   4320
GCGGTTAGCT CCTTCGGTCC TCCGATCGTT GTCAGAAGTA AGTTGGCCGC AGTGTTATCA   4380
CTCATGGTTA TGGCAGCACT GCATAATTCT CTTACTGTCA TGCCATCCGT AAGATGCTTT   4440
TCTGTGACTG GTGAGTACTC AACCAAGTCA TTCTGAGAAT AGTGTATGCG GCGACCGAGT   4500
TGCTCTTGCC CGGCGTCAAT ACGGGATAAT ACCGCGCCAC ATAGCAGAAC TTTAAAAGTG   4560
CTCATCATTG GAAAACGTTC TTCGGGGCGA AAACTCTCAA GGATCTTACC GCTGTTGAGA   4620
TCCAGTTCGA TGTAACCCAC TCGTGCACCC AACTGATCTT CAGCATCTTT TACTTTCACC   4680
AGCGTTTCTG GGTGAGCAAA AACAGGAAGG CAAAATGCCG CAAAAAAGGG AATAAGGGCG   4740
ACACGGAAAT GTTGAATACT CATACTCTTC CTTTTTCAAT ATTATTGAAG CATTTATCAG   4800
GGTTATTGTC TCATGAGCGG ATACATATTT GAATGTATTT AGAAAAATAA ACAAATAGGG   4860
GTTCCGCGCA CATTTCCCCG AAAAGTGCCA CCTGACGTCT AAGAAACCAT TATTATCATG   4920
ACATTAACCT ATAAAAATAG GCGTATCACG AGGCCCTTTC GTC                     4963
```

TIGHT CONTROL OF GENE EXPRESSION IN EUCARYOTIC CELLS BY TETRACYCLINE-RESPONSIVE PROMOTERS

FIELD OF THE INVENTION

The present invention is in the field of molecular biology. In particular, the present invention relates to a polynucleotide molecule coding for a fusion protein comprising a prokaryotic tet repressor and a protein capable of activating transcription in eucaryotes, for example, the acidic domain of virion protein 16 of herpes simplex virus. The invention also relates to the use of this polynucleotide molecule in a method to regulate the expression of a heterologous gene sequence which is operably linked to a minimal promoter comprising, for example, a part of the cytomegalovirus promoter IE and at least one tet operator sequence.

BACKGROUND OF THE INVENTION

The study of gene function in complex genetic environments such as eucaryotic cells would greatly profit from systems that would allow stringent control of the expression of individual genes. Ideally, such systems would not only mediate an "on/off" situation of gene activity but also would permit limited expression at a defined level.

Attempts to control gene activity by various inducible eucaryotic promoters responsive to, for example, heavy metal ions (Mayo et al., *Cell* 29:99–108 (1982); Brinster et al., *Nature (London)* 296:39–42 (1982); Searle et al., *Mol. Cell. Biol.* 5:1480–1489 (1985)), heat shock (Nouer, L. in *Heat Shock Response* (1991), ed. Nover, L., CRC, Boca Raton, Fla. (1991), pp. 167–220), or hormones (Lee et al., *Nature (London)* 294:228–232 (1981); Hynes et al., *Proc. Natl. Acad. Sci. USA* 78:2038–2042 (1981); Klock et al., *Nature (London)* 329:734–736 (1987); Israel & Kaufman, *Nucleic Acids Res.* 7:2589–2604 (1989)) have generally suffered from leakiness of the inactive state (e.g., the metallothionein promoter (Mayo et al., *Cell* 29:99–108 (1982)) or from pleiotropic effects caused by the inducing principles themselves, such as elevated temperature or glucocorticoid hormone action (Lee et al., *Proc. Natl. Acad. Sci. USA* 85:1204–1208 (1988)).

In search of regulatory systems that do not rely on endogenous control elements, several groups have demonstrated that the lac repressor/operator/inducer system of *Escherichia coli* functions in eucaryotic cells. Three basically different approaches have been described: (i) prevention of transcription initiation by properly placed lac operators at promoter sites (Hu & Davidson, *Cell* 48:555–566 (1987); Brown et al., *Cell* 49:603–612 (1987); Figge et al., *Cell* 52:713–722 (1988); Fuerst et al., *Proc. Natl. Acad. Sci. USA* 86:2549–2553 (1989); Deuschle et al., *Proc. Natl. Acad. Sci. USA* 86:5400–5405 (1989)), (ii) blockage of transcribing RNA polymerase II during elongation by a lac repressor/operator complex (lac R/O; Deuschle et al., *Science* 248:480–483 (1990)), and (iii) activation of a promoter responsive to a fusion between lacR and the activating domain of virion protein 16 (VP16) of herpes simplex virus (HSV) (Labow et al., *Mol. Cell. Biol.* 10:3343–3356 (1990); Baim et al., *Proc. Natl. Acad. Sci. USA* 88:5072–5076 (1991)).

At present, however, the utility of the lacR/O-based systems in eucaryotic cells is limited since the inducer isopropyl β-D-thiogalactopyranoside (IPTG), despite its rapid uptake and intracellular stability (Wyborski & Short, *Nucleic Acids Res.* 19:4647–4653), acts rather slowly and inefficiently, resulting in only moderate induction. Nevertheless, an interesting conditional mutant of a lacR-VP16 fusion has been described (Baim et al., *Proc. Natl. Acad. Sci. USA* 88:5072–5076 (1991)). It activates a minimal promoter ≈1000-fold at elevated temperatures in the presence of IPTG. The temperature dependence and the inherent IPTG-related problems, however, may once again limit this approach.

SUMMARY OF THE INVENTION

Control elements of the tetracycline-resistance operon encoded in Tn10 of *Escherichia coli* have been utilized to establish a highly efficient regulatory system in eucaryotic cells. By fusing the tet repressor (tetR) with the activating domain of virion protein 16 (VP16) of herpes simplex virus (HSV), a tetracycline-controlled transactivator (tTA) was generated that is constitutively expressed in HeLa cells. This transactivator stimulates transcription from a minimal promoter sequence derived form the human cytomegalovirus promoter IE combined with tet operator (tetO) sequences. Upon integration of a luciferase gene controlled by a tTA-dependent promoter into a tTA-producing HeLa cell line, high levels of luciferase expression were monitored. These activities are sensitive to tetracycline. Depending on the concentration of the antibiotic in the culture medium (0–1 μg/ml), the luciferase activity can be regulated over up to five orders of magnitude. Thus, the system not only allows differential control of the activity of an individual gene in eucaryotic cells but also is suitable for creation of "on/off" situations for such genes in a reversible way.

In particular, the invention relates to a first polynucleotide molecule coding for a transactivator fusion protein comprising a prokaryotic tet repressor and a protein capable of activating transcription in eucaryotes, for example, the acidic domain of virion protein 16 of herpes simplex virus.

The present invention also relates to a second polynucleotide molecule coding for a protein, wherein said polynucleotide is operably linked to a minimal promoter comprising, for example, a portion of the cytomegalovirus promoter IE operably linked to at least one tet operator sequence.

The invention also relates to vectors comprising the polynucleotide molecules of the invention.

The invention also relates to eucaryotic cells and transgenic organisms transfected with the polynucleotide molecules of the invention.

The invention also relates to a method to down regulate the expression of a protein coded for by a polynucleotide, comprising cultivating the eucaryotic cell of the invention in a medium comprising tetracycline or a tetracycline analogue.

The invention also relates to a method to up regulate the expression of a protein coded for by a polynucleotide, comprising cultivating the eucaryotic cell of the invention in a medium lacking tetracycline or a tetracycline analog.

The invention also relates to a kit comprising a carrier means having in close confinement therein at least two container means such as tubes, vials, bottles and the like, each of which containing a polynucleotide molecule which can be used in the practice of the invention. The invention also relates to kits comprising a eucaryotic cell transfected with the first polynucleotide molecule of the invention.

The polynucleotides described in this invention and cell lines containing said polynucleotides are research tools which allow one to tightly and quantitatively control the expression of a large variety of genes. This is of interest in broad areas of basic as well as applied research.

The invention also relates to the construction of eucaryotic production cell lines and strains in which the synthesis of the product is controlled by the tet regulatory system. These cell lines and strains allow one to induce protein synthesis at a predetermined time point or within a time window during a fermentation process. This control allows one to synthesize in large scale cultures gene products whose prolonged presence is lethal to the cells.

The invention also relates to the construction of cell lines which can be used in screening systems to identify compounds of pharmaceutical or other commercial value. In such systems, the expression of target molecules including but not limited to receptors such as the GABA or estrogen receptor, whose long term presence, in particular, in high copy numbers is often cell damaging, can be temporarily and quantitatively controlled.

The invention also relates to the construction of transgenic animals in which the expression of a single gene can be controlled externally by the tet regulatory system. Such genes include human genes whose expression, failure of expression or other defects are involved in human diseases. Such transgenic animals can serve as models for human diseases in therapeutic studies and for the screening of compounds of pharmaceutical interest.

The invention also relates to the construction of transgenic animals for the production of compounds of pharmaceutical or other commercial interest. For example, by specifically adapting the tet regulatory system to the milk whey expression pathway production of compounds of pharmaceutical or other commercial interest may be obtained within the milk harvest of such animals. By controlling tTA for example via a milk whey specific promoter and the gene of interest via a $P_{CMV*-1}$ type promoter a temporally defined production of such compounds can be achieved.

The initial results regarding this invention were published by the present inventors in *Proc. Natl. Acad. Sci. USA* 89:5547–5551 (June, 1992).

BRIEF DESCRIPTION OF THE FIGURES

FIG. 1A: Diagrammatic representation of the two tTA proteins. In both fusion proteins, tTA and $tTA_s$, the original 207-amino-acid sequence of tetR is conserved. Two versions of VP16 sequences encoding the activation domain were fused in frame to the 3' end of the tetR gene, resulting in tTA, which contains SEQ ID NO: 2, and $tTA_s$, which contains SEQ ID NO: 3. The bold letters indicate the original amino acids at the N terminal end, the junction, and the C-terminal end of the fusion proteins; the other letters designate amino acids introduced due to sequence constraints of the particular system. The numbers delineate amino acid positions within tetR (Hillen and Wissman in *Protein-Nucleic Acid Interaction*, Topics in Molecular and Structural Biology, Saenger and Heinemann (eds.), Vol 10, pp. 143–162 (1989)) or VP16 (Treizenberg et al., *Genes Dev.* 2:718–729 (1988)), respectively.

FIG. 1B: The tTA-dependent transcriptional unit consists of the simian virus 40 (SV40) poly(A) site ($A_n$), the luciferase gene (luc), the $P_{CMV*-1}$ or $P_{hCMV-2}$ containing SEQ ID NO: 5 (encompassing the sequence of nucleic acids from position −52 to −34) and SEQ ID NO: 6 (encompassing the sequence of nucleic acids from position −34 to −23). The two promoters encompass the sequence between +75 and −53 of the $P_{hCMV}$, with one base-pair exchange at −31, which creates a Stu I cleavage site. The Xho I site introduced at −53 by PCR was utilized to insert the heptamerized tetO sequence; see SEQ ID NO: 7. This heptameric sequence is flanked at one side by an 18-nucleotide polylinker, which allows the insertion of the operators in both orientations as Sal I/Xho I fragments. The position of the central G/C base pair of the promoter proximal operator to position +1 is −95 for $P_{CMV*-1}$ (upper construct) and −76 for $P_{CMV*-2}$ (lower construct). The plasmids that contain the four constructs are indicated on the far right.

FIG. 2A: Western blot analysis of electrophoretically separated extracts (6% acrylamide/0.1% SDS gels) with tetR-specific antibodies reveals a protein of about 37 kDa (tTA) in cytoplasmic (C) and nuclear (N) extracts in pUHD15-1 transfected cells (+) that is not present in mock-transfected cells (−).

FIG. 2B: Mobility change of tetO DNA by tTA binding from HeLa cell nuclear extracts. Radioactively labeled tetO DNA was mixed with extracts from mock-transfected (lanes 2 and 3) and pUHD15-1-transfected (lanes 4 and 5) HeLa cells in the absence (lanes 2 and 4) and presence (lanes 3 and 5) of 1 μg of tetracycline per ml (added 2 min prior to the addition of the operator). Lane 1 contains labeled operator DNA only.

FIG. 3A: Dependence of luciferase (luc.) activity on tetracycline concentration. HeLa cell clones X1 (dashed line) and T12 previously grown in tetracycline-free medium were seeded with a density of 5000 cells per 35-mm dish and incubated at the tetracycline concentrations indicated. After reaching ≈90% confluency, cells were harvested and assayed for luciferase activity. Data given are the means ±SD of three independent experiments.

FIG. 3B: Kinetics of tetracycline action. X1 cells were grown in 100-mm dishes to ≈80% confluency in the absence or presence (0.1 μg/ml) of tetracycline. At time 0 cells were washed with phosphate-buffered saline and split into smaller culture dishes (1/20th of the initial cultures per 35-mm dish). Half of the cultures remained in tetracycline-free medium (■) and the other half were incubated in the presence of tetracycline (1 μg/ml; □). The X1 culture grown in tetracycline-containing medium was split in the same manner; one half was further incubated in the presence of tetracycline (●), whereas the other half was transferred to tetracycline-free medium (o). At the times indicated, aliquots were harvested and examined for luciferase activity. The slight increase in luciferase activity monitored at 4 hr in the culture containing tetracycline (●) is reproducible and reflects luciferase induction during the washing step.

FIG. 4A and FIG. 4B: The polynucleotide sequence coding for the tTA transactivator. The nucleotide sequence of the complete open reading frame for tTA is shown together with the corresponding amino acid sequence of the encoded protein (SEQ ID NO: 8 and SEQ ID NO: 9).

FIG. 5A and FIG. 5B: The polynucleotide sequence coding for the tTAs transactivator. The nucleotide sequence of the complete open reading frame for tTAs is shown together with the corresponding amino acid sequence of the encoded protein (SEQ ID NO: 10 and SEQ ID NO: 11).

FIG. 6: The polynucleotide sequence of $P_{hCMV*-1}$. The nucleotide sequence shown (SEQ ID NO: 12) encompasses the tet operator sequences (italics) and the hCMV minimal promoter, of which position −53, the TATA box and position +75 (relative to the transcription start site) are underlined.

FIG. 7: The polynucleotide sequence of $P_{hCMV*-2}$. The nucleotide sequence shown (SEQ ID NO: 13) encompasses the tet operator sequences (italics) and the hCMV minimal promoter, of which position −53, the TATA box and position +75 (relative to the transcription start site) are underlined.

FIG. 8: The polynucleotide sequence of $P_{Tk*-1}$. The nucleotide sequence shown (SEQ ID NO: 14) encompasses the tet operator sequences (italics) and the HSVTk minimal promoter, of which position −81, the TATA box and position +7 (relative to the transcription start site) are underlined.

FIG. 9A, FIG. 9B, and FIG. 9C: The polynucleotide sequence of the cDNA coding for the rabbit progesterone receptor under control of $P_{CMV*-1}$ (SEQ ID NO: 15).

FIG. 10A and FIG. 10B: The polynucleotide sequence of the cDNA coding for the human estrogen receptor under control of $P_{CMV*-1}$ (SEQ ID NO: 16).

DESCRIPTION OF THE PREFERRED EMBODIMENTS

Definitions

Figure 1A:
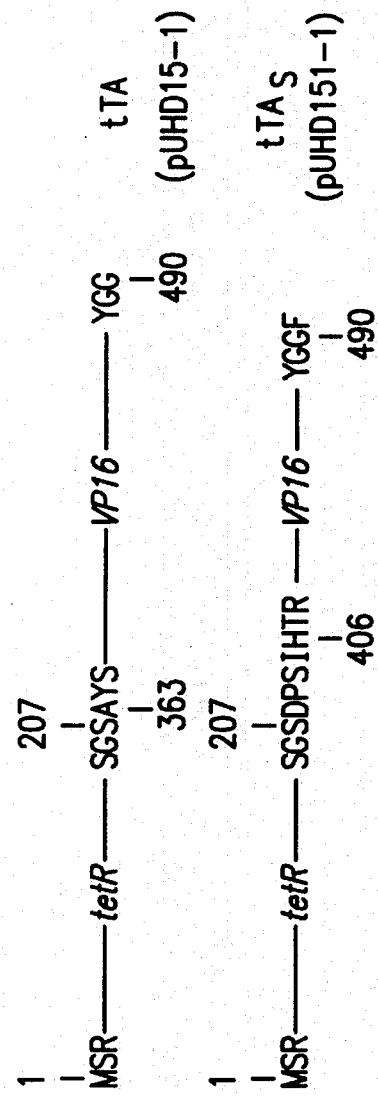
FIG. 1A and FIG. 1B: Schematic representation of the tetR-VP16 fusion proteins and the tTA-dependent transcription unit.

In the description that follows, a number of terms used in recombinant DNA technology are utilized extensively. In order to provide a clear and consistent understanding of the specification and claims, including the scope to be given such terms, the following definitions are provided.

Cloning vector. A plasmid or phage DNA or other DNA sequence which is able to replicate autonomously in a host cell, and which is characterized by one or a small number of restriction endonuclease recognition sites at which such DNA sequences may be cut in a determinable fashion without loss of an essential biological function of the vector, and into which a DNA fragment may be spliced in order to bring about its replication and cloning. The cloning vector may further contain a marker suitable for use in the identification of cells transformed with the cloning vector.

Expression vector. A vector similar to a cloning vector but which is capable of enhancing the expression of a gene which has been cloned into it, after transformation into a host. The cloned gene is usually placed under the control of (i.e., operably linked to) certain control sequences such as promoter sequences. Promoter sequences may be either constitutive or inducible.

Eucaryotic Host Cell. According to the invention, a eucaryotic host cell may be any such cell which include, but are not limited to, yeast, plant cells, insect cells, e.g. Schneider and Sf9 cells; mammalian cells, e.g. lymphoid and HeLa cells (human), NIH3T3 and embryonic stem cells (murine), and RK13 (rabbit) cells.

Recombinant Eucaryotic Host. According to the invention, a recombinant eucaryotic host may be any eucaryotic cell which contains the polynucleotide molecules of the present invention on an expression vector or cloning vector. This term is also meant to include those eucaryotic cells that have been genetically engineered to contain the desired polynucleotide molecules in the chromosome, genome or episome of that organism. Thus, the recombinant eucaryotic host cells are capable of stably or transiently expressing the proteins.

Recombinant vector. Any cloning vector or expression vector which contains the polynucleotide molecules of the invention.

Host. Any prokaryotic or eucaryotic cell that is the recipient of a replicable vector. A "host," as the term is used herein, also includes prokaryotic or eucaryotic cells that can be genetically engineered by well known techniques to contain desired gene(s) on its chromosome or genome. For examples of such hosts, see Sambrook et al., *Molecular Cloning: A Laboratory Manual*, Second Edition, Cold Spring Harbor Laboratory, Cold Spring Harbor, N.Y. (1989).

Promoter. A DNA sequence generally described as the 5' region of a gene, located proximal to the start codon. The transcription of an adjacent gene(s) is initiated at the promoter region. If a promoter is an inducible promoter, then the rate of transcription increases in response to an inducing agent. In contrast, the rate of transcription is not regulated by an inducing agent if the promoter is a constitutive promoter.

Minimal Promoter. A partial promoter sequence which defines the transcription start site but which by itself is not capable, if at all, of initiating transcription efficiently. The activity of such minimal promoters depend on the binding of activators such as a tetracycline-controlled transactivator to operably linked binding sites.

Gene. A DNA sequence that contains information needed for expressing a polypeptide or protein.

Structural gene. A DNA sequence that is transcribed into messenger RNA (mRNA) that is then translated into a sequence of amino acids characteristic of a specific polypeptide.

Polynucleotide molecules A polynucleotide molecule may be a polydeoxyribonucleic acid molecule (DNA) or a polyribonucleic acid molecule (RNA).

Complementary DNA (cDNA). A "complementary DNA," or "cDNA" gene includes recombinant genes synthesized by reverse transcription of mRNA and from which intervening sequences (introns) have been removed.

Expression. Expression is the process by which a polypeptide is produced from a structural gene. The process involves transcription of the gene into mRNA and the translation of such mRNA into polypeptide(s).

Fragment. A "fragment" of a molecule is meant to refer to any polypeptide subset of that molecule.

Tetracycline Analogue. A "tetracycline analogue" is any one of a number of compounds that are closely related to tetracycline and which bind to the tet repressor with a $K_a$ of at least about $10^6 M^{-1}$. Preferably, the tetracycline analogue binds with an affinity of about $10^9 M^{-1}$ or greater, e.g. $10^{11} M^{-1}$. Examples of such tetracycline analogues include, but are not limited to those disclosed by Hlavka and Boothe, "The Tetracyclines," in *Handbook of Experimental Pharmacology* 78, R. K. Blackwood et al. (eds.), Springer-Verlag, Berlin-New York, 1985; L. A. Mitschef, "The Chemistry of the Tetracycline Antibiotics," *Medicinal Research* 9, Dekker, New York, 1978; Noyee Development Corporation, "Tetracycline Manufacturing Processes," *Chemical Process Reviews*, Park Ridge, N.J., 2 volumes, 1969; R. C. Evans, "The Technology of the Tetracyclines," *Biochemical Reference Series* 1, Quadrangle Press, New York, 1968; and H. F. Dowling, "Tetracycline," *Antibiotics Monographs*, no. 3, Medical Encyclopedia, New York, 1955; the contents of each of which are fully incorporated by reference herein.

The present invention relates to a control system that in eucaryotic cells allows regulation of expression of an individual gene over up to five orders of magnitude. This system is based on regulatory elements of a tetracycline-resistance operon, e.g. Tn/10 of *E. coli* (Hillen & Wissmann, "Topics in Molecular and Structural Biology," in *Protein-Nucleic Acid Interaction*, Saeger & Heinemann, eds., Macmillan, London, 1989, Vol. 10, pp. 143–162), in which transcription of resistance-mediating genes is negatively regulated by a tetracycline repressor (tetR). In the presence of tetracycline or a tetracycline analogue, tetR does not bind to its operators located within the promoter region of the operon and allows transcription. By combining tetR with a protein domain capable of activating transcription in eucaryotes, such as (i) acidic domains (e.g. the C-terminal domain of VP16 from HSV (Triezenberg et al., *Genes Dev.* 2:718–729 (1988)) or empirically determined, noneucaryotic acidic domains identified by genetic means (Giniger and Ptashne, *Nature* 330:670–672 (1987))) or (ii) proline rich domains (e.g. that of CTF/NF-1 (Mermod et al., *Cell* 58:741–753 (1989))) or (iii) serine/threonine rich domains (e.g. that of Oct-2 (Tanaka and Herr, *Cell* 60:375–386 (1990))) or (iv) glutamine rich domains (e.g. that of Sp1 (Courey and Tjian, *Cell* 55:867–898 (1988))) a hybrid transactivator is generated that stimulates minimal promoters fused to tetracycline operator (tetO) sequences. These promoters are virtually silent in the presence of low concentrations of tetracycline, which prevents the tetracycline-controlled transactivator (tTA) from binding to tetO sequences.

The specificity of the tetR for its operator sequence (Hillen & Wissmann, "Topics in Molecular and Structural Biology," in *Protein-Nucleic Acid Interaction*, Saeger & Heinenann, eds., Macmillan, London, 1989, Vol. 10, pp. 143–162) as well as the high affinity of tetracycline for tetR (Takahashi et al., *J. Mol. Biol.* 187:341–348 (1986)) and the well-studied chemical and physiological properties of tetracyclines constitute a basis for an inducible expression system in eucaryotic cells far superior to the lacR/O/IPTG system. This has already been demonstrated in plant cells, in which direct repressor action at promoter sites is efficiently reversed by the antibiotic (Gatz & Quail, *Proc. Natl. Acad. Sci. USA* 85:1394–1397 (1988); Gatz et al., *Mol. Gen. Genet* 227:229–237 (1991)).

In particular, the invention relates to a first polynucleotide molecule coding for a transactivator fusion protein comprising the tet repressor (tetR) and a protein capable of activating transcription in eucaryotes. The polynucleotide coding for tetR may be obtained according to Postle et al., *Nucl. Acids Res.* 2:4849–4863 (1984), the contents of which are fully incorporated by reference herein. Other tetR sequences and the respective binding sites for these repressors are identified (Waters et al., *Nucl. Acids Res.* 11:6089–6105 (1983); Postle et al., *Nucl. Acids Res.* 12:4849–4863 (1984); Unger et al., *Gene* 31:103–108 (1984); Unger et al., *Nucl. Acids Res.* 12:7693–7703 (1984); Tovar et al., *Mol. Gen. Genet.* 215:76–80 (1988); for comparison and overview see Hillen and Wissmann in *Protein-Nucleic Acid Interaction*, Topics in Molecular and Structural Biology, Saenger and Heinemann (eds.), Macmillan, London, Vol. 10, pp. 143–162 (1989)) and can also be utilized for the expression system described.

The polynucleotide coding for the negatively charged C-terminal domain of HSV-16, a protein known to be essential for transactivation in eucaryotes, may be obtained according to Triezenberg et al., *Genes Dev.* 2:718–729 (1988), the contents of which are fully incorporated by reference herein. Preferably, the activating domain comprises the C-terminal 130 amino acids of the virion protein 16.

The polynucleotide molecule coding for tetR may be linked to a polynucleotide molecule ceding for the activating domain of HSV-16 and recombined with vector DNA in accordance with conventional techniques, including blunt-ended or stagger-ended termini for ligation, restriction enzyme digestion to provide appropriate termini, filling in of cohesive ends as appropriate, alkaline phosphatase treatment to avoid undesirable joining, and ligation with appropriate ligases.

Preferably, the polynucleotide molecule coding for the transactivator fusion protein further comprises an operably linked promoter. The promoter may be an inducible promoter or a constitutive promoter. Examples of such promoters include the human cytomegalovirus promoter IE as taught by Boshart et al., *Cell* 41:521–530 (1985), ubiquitously expressing promoters such as HSV-Tk (McKnight et al., *Cell* 37:253–262 (1984) and β-actin promoters (e.g. the human β-actin promoter as described by Ng et al., *Mol. Cell. Biol.* 5:2720–2732 (1985)), as well as promoters in combination with control regions allowing integration site independent expression of the transgene (Grosveld et al., *Cell* 51:975–985 (1987), as well as tissue specific promoters such as albumin (liver specific; Pinkert et al., *Genes Dev.* 1:268–277 (1987)), lymphoid specific promoters (Calame and Eaton, *Adv. Immunol.* 43:235–275 (1988); in particular promoters of T-cell receptors (Winoto and Baltimore, *EMBO J.* 8:729–733 (1989)) and immunoglobulins; Banerji et al. , *Cell* 33:729–740 (1983); Queen and Baltimore, ibid. 741–748), neuron specific promoters (e.g. the neurofilament promoter; Byrne and Ruddle, *Proc. Natl. Acad. Sci. USA* 86:5473–5477 (1989)), pancreas specific promoters (Edlund et al., *Science* 230:912–916 (1985)) or mammary gland specific promoters (milk whey promoter, U.S. Pat. No. 4,873,316 and European Application Publication No. 264, 166) as well as developmentally regulated promoters such as the murine hox promoters (Kessel and Gruss, *Science* 249:374–379 (1990)) or the α-fetoprotein promoter (Campes and Tighman, *Genes Dev.* 3:537–546 (1989)), the contents of each of which are fully incorporated by reference herein. Preferably, the promoter is constitutive in the respective cell types.

The invention also relates to a second polynucleotide molecule coding for a protein, wherein said polynucleotide is operably linked to a minimal promoter operatively linked to at least one tet operator (tetO) sequence. The tetO sequence may be obtained, for example, according to Hillen & Wissmann, "Topics in Molecular and Structural Biology," in *Protein-Nucleic Acid Interaction*, Saeger & Heinemann, eds., Macmillan, London, 1989, Vol. 10, pp. 143–162, the contents of which are fully incorporated by reference herein. Other tetO sequences which may be used in the practice of the invention may be obtained from the references given in the following (Waters et al., *Nucl. Acids Res.* 11:6089–6105 (1983); Postle et al., *Nucl. Acids Res.* 12:4849–4863 (1984); Unger et al., *Gene* 31:103–108 (1984); Unger et al., *Nucl. Acids Res.* 12:7693–7703 (1984); Tovar et al., *Mol. Gen. Genet.* 215:76–80 (1988); for comparison and overview see Hillen and Wissmann in *Protein-Nucleic Acid Interaction*, Topics in Molecular and Structural Biology, Saenger and Heinemann (eds.), Macmillan, London, Vol. 10, pp. 143–162 (1989)), the disclosures of which are fully incorporated by reference herein in their entirety. One, two, three, four, five, six, seven, eight, nine or ten or more copies of the tet operator sequence may be employed, with a greater number of such sequences allowing an enhanced range of regulation. As shown in the Examples, multiple copies of the tet operator sequence provides a synergistic effect on the ability to control expression of the heterologous protein.

The polynucleotide sequence specifying the cytomegalovirus promoter may be obtained according to Boshart et al., *Cell* 41:521–530 (1985), the contents of which are fully incorporated by reference herein. Preferably, positions +75 to −53 or +75 to −31 of the promoter-enhancer may be employed. The promoter may be followed by a polylinker and then by the gene coding for the protein of interest. While the luciferase gene or other reporter gene, e.g. the gene coding for chloramphenicol acetyltransferase or βgalactosidase, may be used to demonstrate the operability of the regulatory system, the invention is not intended to be so limited.

The invention further relates to homologous and heterologous genes involved in developmental and differentiation processes, as well as in metabolic pathways ensuring cellular function and communication. It relates furthermore to cellular systems utilized in the production of substances of commercial interest, including, but not limited to immunoglobulins, components of the cytoskeleton, cell adhesion proteins, receptors, cytokines peptide hormones and enzymes.

As an example for a gene, whose product is of considerable scientific and commercial interest, the cDNA of the α1 subunit of the GABA receptor was placed under the control of the tet regulatory system as follows.

Figure 1B:
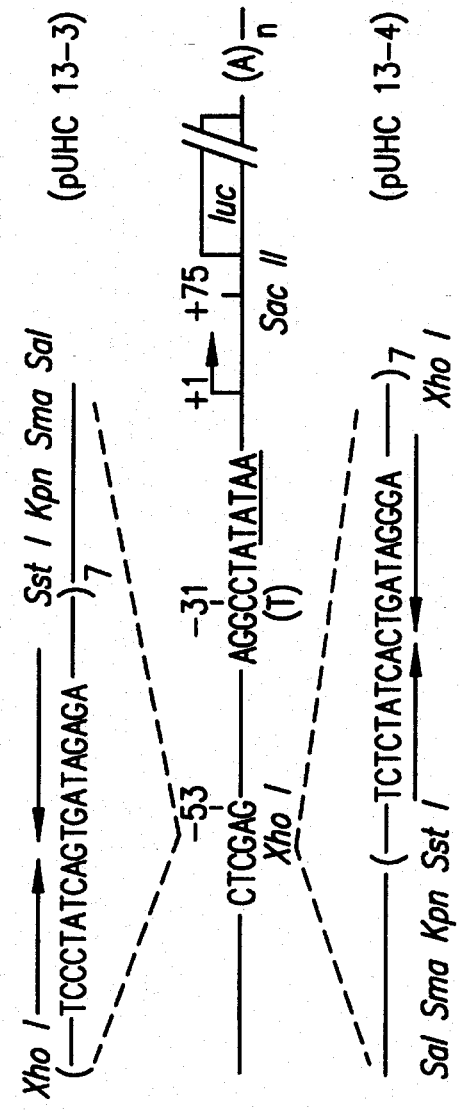

Plasmid pRK5GABAα1 (gift of P. H. Seeburg) contains the cDNA derived coding sequence for the α1 subunit of the GABA receptor (GenBank accession #L08490, see Seeburg et al., *Cold Spring Harb Symp Quant Biol.* 55:29–40 (1990)) under the control of the human cytomegalovirus promoter ($P_{hCMV}$). Treatment of purified pRK5GABAα1 DNA with restriction endonuclease Ec1136II removes the entire sequence of $P_{hCMV}$ upstream of position −16 (position +1 being the transcriptional start site) due to the presence of two cleavage sites of this enzyme in the plasmid. The same restriction endonuclease was utilized for recovering a 335 bp fragment from plasmid pUHC13-4 (FIG. 1b). This fragment spans the sequence of $P_{hCMV*-2}$ (FIG. 7) upstream of position −16 up to position −351 of pUHC13-4, and contains the major part of $P_{hCMV*-2}$, in particular the tet operator sequences (FIG. 1b). This fragment was ligated with the DNA prepared from pRK5GABAα1 containing the coding sequence of the α1 GABA subunit and transformed into *E. coli* C600. Plasmids recovered from ampicillin resistant colonies were analyzed and those showing the expected restriction cleavage pattern were verified by sequence analysis. The resulting plasmid GABAα1 which contains the GABAα1 coding sequence under the control of $P_{CMV*-2}$ was transfected into the HtTA-1 cell line, stably expressing tTA (FIG. 1a). The expression of the α1 subunit of the GABA receptor in the HtTA-1 cell line was demonstrated by indirect immunofluorescence in situ. This immunofluorescence was abolished by addition of tetracycline to the medium at a final concentration of 0.1 μg/ml, demonstrating the tetracycline controlled expression of the α1 subunit of the GABA receptor in HeLa cells.

In a similar cloning strategy the cDNAs of the rabbit progesterone receptor (Loosfelt et al., *Proc. Natl. Acad. Sci. USA* 83:9045–9049 (1986)) was placed under the control of $P_{CMV*-1}$, resulting in the tetracycline regulated expression vector pUHDpgr-3 containing the nucleotide sequence depicted in FIGS. 9A–9C.

In a similar cloning strategy the cDNAs of the human estrogen receptor (Green et al., *Nature* 320:134–139 (1986)) was placed under the control of $P_{CMV*-1}$, resulting in the tetracycline regulated expression vector pUHDher-3 containing the nucleotide sequences depicted in FIGS. 10A–B.

In both plasmids, the boundaries between the cDNA insert and the vector were verified by DNA sequence analysis.

Using a similar cloning strategy, the cDNAs of the X-protein of HBV (Tiollais et al., *Nature* 317:489–495 (1985)), may be placed under the control of $P_{CMV*-1}$.

The present invention also relates to eucaryotic cells transfected with the polynucleotide molecules of the present invention. In particular, the invention relates to eucaryotic cells transfected with (a) a first polynucleotide molecule coding for a transactivator fusion protein comprising a prokaryotic tet repressor and a protein capable of activating transcription in eucaryotes; and (b) a second polynucleotide molecule coding for a protein, wherein said second polynucleotide molecule is operably linked to a minimal promoter and at least one tet operator sequence.

The two polynucleotide molecules may reside on the same or separate vectors. In a preferred embodiment, the first polynucleotide is integrated into the chromosome of a eucaryotic cell or transgenic animal and the second polynucleotide is introduced as part of a vector. Integration may be achieved where there is crossover at regions of homology shared between the incoming polynucleotide molecule and the particular genome.

The expression of the heterologous protein from such transfected eucaryotic cells may be tightly regulated. Unexpectedly, it has been determined that the expression system of the present invention may be used to regulate expression by about 5 orders of magnitude. In addition, it has been discovered that the expression system of the present invention allows one to rapidly turn on and off the expression of the heterologous gene in a reversible way. Moreover, it has been discovered that the expression system of the invention allows one to achieve a desired level of expression according to how much tetracycline or tetracycline analogue is employed (see FIG. 3). Thus, the expression system of the present invention is a great advance in the art.

The invention also relates to transgenic animals comprising one or two of the polynucleotide molecules of the present invention. Such transgenic animals may be obtained, for example, by injecting the polynucleotide into a fertilized egg which is allowed to develop into an adult animal. In particular, a few hundred DNA molecules are injected into the pro-nucleus of a fertilized one cell egg. The microinjected eggs are then transferred into the oviducts of pseudopregnant foster mothers and allowed to develop. It has been reported by Brinster et al., *Proc. Natl. Acad. Sci. USA* 82:4438–4442 (1985), the contents of which are fully incorporated by reference herein, that about 25% of mice which develop will inherit one or more copies of the microinjected DNA. Alternatively, the transgenic animals may be obtained by utilizing recombinant ES cells for the generation of the transgenes, as described by Gossler et al., *Proc. Natl. Acad. Sci. USA* 83:9065–9069 (1986), the contents of which are fully incorporated by reference herein. Animals transgenic for the gene encoding a tetR/transcriptional activator domain fusion protein under the transcriptional control of one of the promoter sequences described above and/or the gene under control of this regulatory protein can be generated e.g. by the coinjection of the two polynucleotide molecules. Alternatively, independent animal lines transgenic for only one of the polynucleotides described can be generated in a first step:

(i) Animals transgenic only for the gene to be controlled by the transactivator can be screened for the desired non-activated expression level. This includes indicator animals transgenic for a reporter gene (e.g. cat, luc, lacZ) under transcriptional control of the tetR/transcriptional activator domain fusion protein dependent minimal promoter, which are easy to screen for integration sites showing the desired, in general a low level basal expression. If advantageous, this empirical determined loci can be used subsequently for a homologous recombination approach (Mansour et al., *Nature* 336:348–352 (1988)), by which the reporter gene is substituted by a respective gene of interest in the previously analyzed integration site.

(ii) Animals transgenic only for a gene encoding a tetR/transcriptional activator domain fusion protein can be analyzed for the desired expression pattern of the regulator protein, whenever tissue specific promoters were utilized for the expression of the respective regulator gene. This approach will result in a series of animals expressing the regulator protein in different tissues, allowing a choice between different geno- and phenotypical backgrounds as a basis for the further experiments.

Subsequently, the desired double transgenic animals are obtained by breeding the two complementary transgenic animal lines. As one example, it is possible to prepare a polynucleotide molecule comprising a milk protein promoter and microinject the DNA into the fertilized egg to give, upon development, a transgenic mammal which is capable of producing the heterologous protein in its milk, when in the absence of tetracycline or a tetracycline analog. See International Application Publication No. WO 88/00239 and European Application Publication No. 0 264 166, the contents of which are fully incorporated by reference herein.

According to the second approach, the independent generation of (i) reporter mice and (ii) transactivator nice with subsequent breeding towards double transgenic animals, the following experiments were performed:

(i) A 3.1 kbp XhoI/EaeI fragment of pUHC13-3 (see FIG. 1*b*) was injected into the pro-nucleus of fertilized mice eggs essentially as described by Brinster et al., *Proc. Natl. Acad. Sci. USA* 82:4438–4442 (1985). The injected polynucleotide comprises $P_{hCMV*-1}$, the luciferase gene and the SV40 intron/polyadenylation signal. The offspring were analyzed for the integration of the transgene by isolating genomic DNA from tail tissue and the pUHC13-3 fragment was identified in the mouse genome by conventional DNA-hybridization techniques (Southern *J. Mol. Biol.* 98:503–517 (1975)). In addition, ear tissue frown DNA-positive mice was cut and primary ear fibroblasts grown in cell culture were analyzed for luciferase activity. The observed activity varied between background values and up to 20 rlu/µg of protein, which is—as expected—a rather low specific activity (for comparison see Table 1), as no transactivator is present in these cells. However, after transiently transfecting plasmid pUHD15-1 (encoding the Tc-controlled transactivator tTA) by the calcium-phosphate technique (Graham and van der Eb, *Virology* 52:456–457 (1973)) into these primary cells, as up to 100 fold stimulation of luciferase activity was observed in several primary cell cultures derived from different mice. This activation was completely abolished by the presence of 1 µg/ml Tc. The respective animals obviously are suitable reporter mice. They are bred to expand the colonies of reporter mice.

(ii) A 2.25 kbp XhoI/HindIII fragment of pUHD15-1 (see the Examples) was injected into the pro-nucleus of fertilized mice eggs essentially as described by Brinster et al., *Proc. Natl. Acad. Sci. USA* 82:4438–4443 (1985). The injected polynucleotide comprises the human cytomegalovirus IE promoter/enhancer, the tTA gene and the SV40 late polyadenylation site. The CMV promoter/enhancer is a well characterized and reliable transcription signal in transgenic mice (Furth et al., *Nuc. Acids Res.* 9:6205–6208 (1991)). The offspring were analyzed for the integration of the transgene by isolating genomic DNA from tail tissue and the pUHD15-1 fragment was identified in the mouse genome by conventional DNA-hybridization techniques (Southern, *J. Mol. Biol.* 98:503–517 (1975)). Animals positive for the tTA gene containing polynucleotide fragment of pUHD15-1 are further bred to expand the colonies of tTA mice.

Crosses between reporter and tTA mice were performed and offspring positive for both, the reporter gene and the transactivator gene, are identified. These mouse lines are further expanded to analyze the Tc dependent regulation phenotype qualitatively and quantitatively.

Figure 3B:
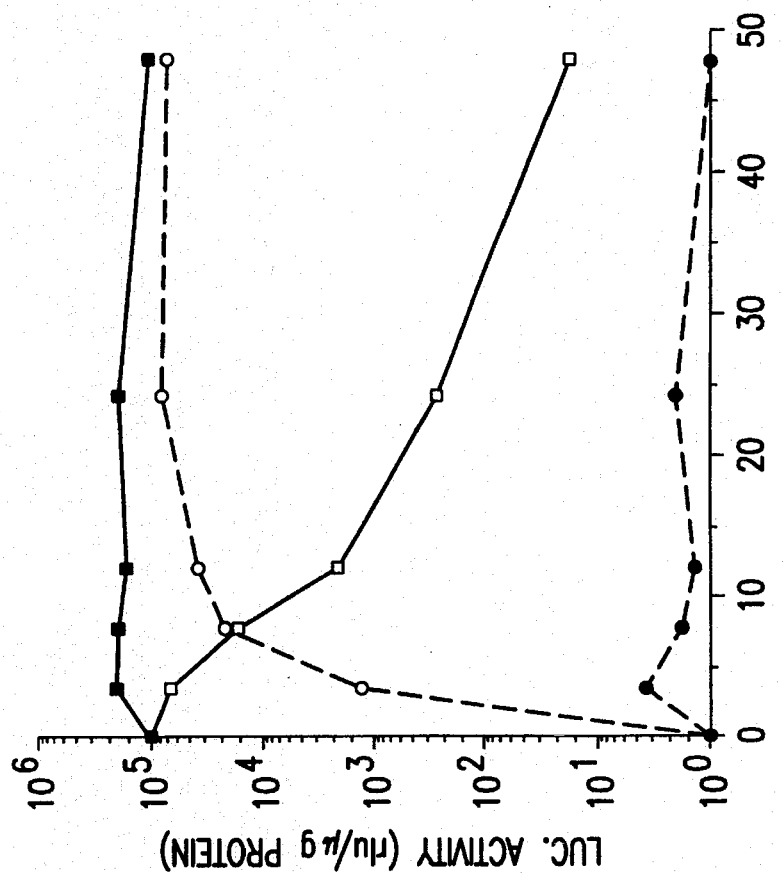
FIG. 3A and FIG. 3B: Graphs showing the dependence of tTA function on tetracycline.
Figure 3A:
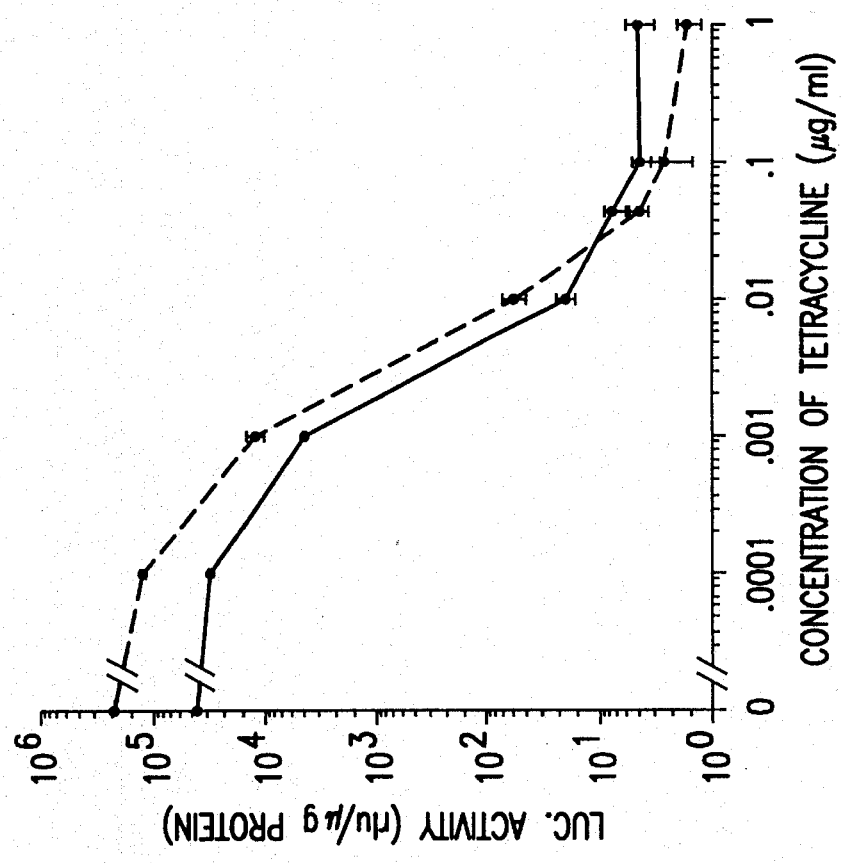

Thus, the invention also relates to a method to down regulate the expression of a protein coded for by a polynucleotide, comprising cultivating the transfected eucaryotic cells of the present invention in a medium comprising tetracycline or a tetracycline analogue. As described in the Examples, it is possible to closely control the extent of expression by carefully controlling the concentration of tetracycline or tetracycline analogue in the culture media. As shown in FIG. 3, panel A, as little as 0.0001 µg/ml of tetracycline will begin to result in a decrease of polypeptide (luciferase) expression. At about 0.1 µg/ml the expression is essentially shut off. The concentration of tetracycline or tetracycline analog which can be used to regulate the expression level may range from about 0.001 to about 1 µg/ml.

The invention also relates to a method to up regulate the expression of a protein coded for by a polynucleotide, comprising cultivating the eucaryotic cells of the present invention in a medium lacking tetracycline or a tetracycline analogue.

Media which may be used in the practice of the invention include any media which are compatible with the transfected eucaryotic cells of the present invention. Such media are commercially available (Gibco/BRL).

Alternatively, it is possible to down regulate the expression of a protein in a transgenic animal of the present invention by administering to the animal tetracycline or tetracycline analogue. The tetracycline or tetracycline analogue may be administered by any means that achieves its intended purpose, e.g. by the oral route. Alternatively, or concurrently, the parenteral, subcutaneous, intravenous, intramuscular, intraperitoneal, transdermal, or buccural routes may be used. The dosage administered will be dependent upon the age, health, and weight of the animal, kind of concurrent treatment, if any, and frequency of treatment. To up regulate the expression of the protein, the administration of tetracycline or tetracycline analogue may then be interrupted.

The invention also relates to a kit comprising a carrier means having in close confinement therein at least two container means such as tubes, vials, bottles and the like, each of which containing a polynucleotide molecule which can be used in the practice of the invention. In particular, the invention relates to a kit comprising a carrier means having in close confinement therein at least two container means, wherein a first container means contains a first polynucleotide molecule coding for a transactivator fusion protein comprising a prokaryotic tet repressor and a protein capable of activating transcription in eucaryotes; and a second container means contains a second polynucleotide molecule comprising a minimal promoter operably linked to at least one tet operator sequence, wherein the second polynucleotide molecule is capable of being ligated to a heterologous gene sequence coding for a polypeptide and activating the expression of the heterologous protein.

The invention also relates to kits comprising a carrier means having in close confinement therein at least two container means, wherein a first container means contains a eucaryotic cell transfected with a first polynuclcotide molecule coding for a transactivator fusion protein comprising a prokaryotic tet repressor and a protein capable of activating transcription in eucaryotes; and a second container means contains a second polynuclcotide molecule comprising a minimal promoter operably linked to at least one tet operator sequence, wherein the second polynucleotide molecule is capable of being ligated to a heterologous gene sequence coding for a polypeptide and activating expression of the polypeptide.

Having now generally described this invention, the same will be understood by reference to the following examples which are provided herein for purposes of illustration only and are not intended to be limiting unless otherwise specified.

EXAMPLES

Materials and Methods

Construction of the Transactivators tTA and tTA$_s$. The tetR sequence was originally recovered from pWH510 (Altschmeid et al., *EMBO J.* 7:4011–4017 (1988), the disclosure of which is fully incorporated by reference herein) by PCR and inserted into pUHD10-1 (Deuschle et al., *Proc. Natl. Acad. Sci. USA* 86:5400–5404 (1989)), resulting in pUHD14-1 (see, the Dissertation of Manfred Gossen, "Prokaryotic Repressor Operator Systems in the Control of Eukaryotic Gene Expression, Heidelberg University, 1993, the contents of which are fully incorporated by reference herein). A unique Afl II cleavage site overlapping the tetR stop codon in this plasmid construct allows for the in-frame insertion of coding sequences. To generate tTA, a 397-basepair (bp) MluI/FokI fragment of pMSVP16 (Triezenberg et al., *Genes Dev.* 2:718–729 (1988), the disclosure of which is fully incorporated by reference herein) coding for the C-terminal 130 amino acids of VP16 of HSV was blunted by filling in the protruding ends with T4 DNA polymerase. This DNA was inserted in pUHD14-1 previously cleaved with Aft II and blunted by mung bean nuclease. The resulting plasmid pUHD15-1 encodes the tTA sequence (FIG. 1, panel a) under the control of the P$_{hCMV}$ (human cytomegalovirus promoter IE; see below). In a homologous approach a DNA fragment coding for the 97-amino acid C-terminal portion of VP16 was fused to tetR by PCR-mediated cloning. The resulting plasmid, pUHD151-1, encodes the smaller version of the trans-activator, tTA$_s$, (FIG. 1, panel a).

Construction of P$_{hCMV*}$ and the Luciferase Reporter Plasmid. Plasmid pUHC13-1 is a derivative of pUHD10-1 (Deuschle et al., *Proc. Natl. Acad. Sci. USA* 86:5400–5404 (1989)). It contains the promoter-enhancer sequence of P$_{hCMV}$, spanning position +75 to position −675 (Boshart et al., *Cell* 41:521–530 (1985)). This promoter is followed by a polylinker and the luciferase gene of *Photinus pyralis* fused to the SV40 small-t intron and poly(A) signal. The latter elements and the luciferase gene were transferred from pSV2L-AΔ5' (DeWit et al., *Mol. Cell. Biol.* 7:725–737 (1987)). By this transfer the N-terminus of luciferase has been modified as described (Deuschle et al., *Proc. Natl. Acad. Sci. USA* 86:5400–5404 (1989)). The enhancer region of P$_{hCMV}$ was removed by PCR-mediated cloning, whereby a Xho I site was introduced adjacent to position −53. The resulting minimal promoter, P$_{hCMV*}$ (FIG. 1, panel b) is part of the reporter plasmid pUHC13-2.

Construction of P$_{hCMV*-1}$ and P$_{hCMV*-2}$. To combine P$_{hCMV*}$ with tet operators, the 19-bp inverted repeat sequence of operator O2 of Tn10 (Triezenberg et al., *Genes Dev.* 2:718–729 (1988)) was synthesized as part of a 42-bp DNA fragment (upper strand: 5' TCGAGTTTACCACTC-CCTATCAGTGATAGAGAAAAGTGAAAG-3' (SEQ ID NO: 1). Upon annealing, the two complementary strands exposed the compatible protruding ends of a Xho I and a Sal I cleavage site at the 5' and 3' ends, respectively. Ligation of this fragment into the Xho I site of the polylinker of pT81-luc (Nordeen, S. K., *BioTechniques* 6:454–457 (1988)) created upon cloning single as well as multiple inserts of operator sequences upstream of a thyroidine kinase (tk) minimal promoter from HSV contained in pT81-luc. tk promoters containing one, two, and seven operator sequences were examined for their ability to be activated in transient expression experiments using the HeLa cell line HtTa-1 (see below). All constructs were active in tTA-producing cells in a tetracycline-dependent manner. The heptameric version of the tetO sequences caused by far the highest activation of all P$_{tk}$-tetO constructs. It therefore was removed as a XhoI/SalI fragment and transferred into pUHC13-2. Due to the asymmetric location of the tetO within the polylinker of pT81-luc, the resulting plasmids pUHC13-3 and pUHC13-4 contain the heptameric tetOs in two orientations differing in the distance between the operators and position +1 of P$_{hCMV}$ by 19 bp. The two tetO-containing promoters were designated P$_{hCMV*-1}$ and P$_{hCMV*-2}$ (FIG. 1, panel b).

Band-Shift Assay. Cytoplasmic and nuclear cell extracts from ≈2×10$^6$ cells were prepared as described by Andrews and Faller, *Nucl. Acids Res.* 19:2499 (1991), except that the cytoplasmic protein fraction was centrifuged once more (1 hr, 100,000×g). Nuclear proteins were extracted by a buffer containing 20 mM Hepes-KOH (pH 7.9), 25% glycerol, 420 mM NaCl, 1.5 mM MgCl$_2$, 0.2 mM EDTA, 0.5 mM dithiothreitol, and 0.5 mM phenylmethylsulfonyl fluoride. Aliquots (5 µl) of nuclear extracts were mixed with 15 µl of binding buffer (10 mM Tris.HCl, pH 7.5/10 mM MgCl$_2$) containing 20 µg of calf thymus DNA, 5 µg of bovine serum albumin, and 2 fmol of $^{32}$P-labeled tetO DNA. The tetO DNA was isolated from pUHC13-3 as a 42-bp Taq I fragment whose protruding ends were filled in by Klenow enzyme in the presence of [α-$^{32}$P]dCTP. After 20 min. at room temperature, aliquots of the binding reaction mixture were loaded onto a 5% polyacrylamide/0.07% bisacrylamide gel. Electrophoresis was carried out in 90 mM Tris base/90 mM boric acid/3 mM EDTA at 5 V/cm.

Luciferase Assays. Cell grown to ≈80% confluency in 35-mm dishes in Eagle's minimum essential medium were washed with 2 ml of phosphate-buffered saline before they were lysed in 25 mM Tris phosphate, pH 7.8/2 mM dithiothreitol/2 mM diaminocyclohexanetetraacetic acid/10% glycerol/1% Triton X-100 for 10 min at room temperature. The lysate was scraped off the culture dishes and centrifuged for 10 see in an Eppendorf centrifuge. Next, aliquots (10 µl) of the supernatant were mixed with 250 µl of 25 mM glycylglycine/15 mM MgSO$_5$/5 mM ATP and assayed for luciferase activity in a Lumat LB9501 (Berthold, Wildbad, F. R. G.) using the integral mode (10 sec). D-Luciferin (L6882, Sigma) was used at 0.5 mM. The background signal measured in extracts of HeLa cells that did not contain a luciferase gene was indistinguishable from the instrumental background [80–120 relative light units (rlu)/10 sec]. Protein content of the lysates was determined according to Bradford (Bradford, M. M., *Anal. Biochem.* 72:248–254 (1976)).

Results

Construction and Characterization of the tTA. To convert the prokaryotic tet repressor into a eukaryotic transactivator it was fused to the negatively charged C-terminal domain of HSV-VP16, known to be essential for transactivation. (Triezenberg et al., *Genes Dev.* 2:718–729 (1988)). Sequences coding for either a 97- or a 127-amino acid C-terminal portion of VP16 were fused to the tetR gene, resulting in the coding sequences of $tTA_s$ and tTA, respectively (FIG. 1, panel a). In plasmids coding for tTA (pUHD15-$tTA_s$ (pUHD151-1) the transactivator sequences are flanked upstream by $P_{hCMV}$ and downstream by the SV40 poly(A) site. The two fusion proteins did not differ in their functional in vivo properties.

Figure 2A:
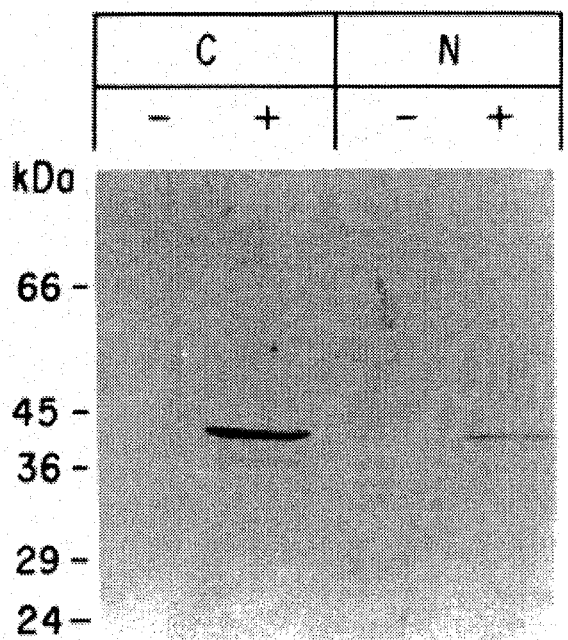
FIG. 2A and FIG. 2B: Western blots showing the identification and characterization of tTA produced in HeLa cells. HeLa cells grown to 40% confluency were transiently transfected with pUHD15-1 by the calcium phosphate method. Nuclear and cytoplasmic extracts were prepared after 36 hr.
Figure 2B:
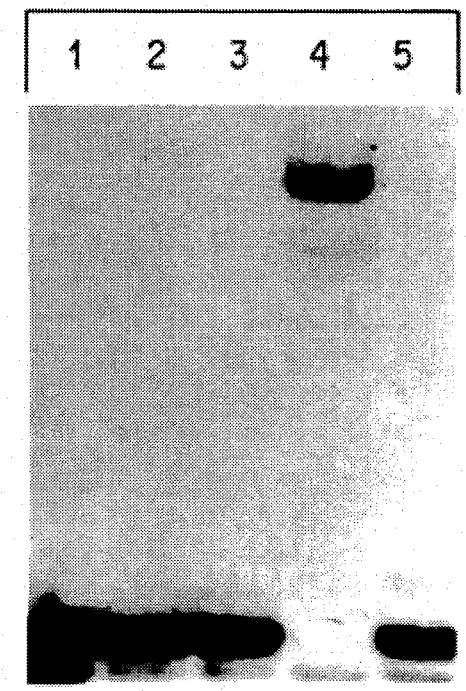

HeLa cells transiently transfected with pUHD15-1 produced a fusion protein of the expected molecular mass (37 kDa), as demonstrated in immunoblots of the electrophoretically separated cytoplasmic and nuclear extracts (FIG. 2, panel a). When nuclear extracts were mixed with the tetO DNA the electrophoretic mobility of the DNA was diminished. The specificity of the interaction between tTA and operator DNA was confirmed by the finding that no mobility change for tetO DNA was detectable in the presence of the specific inducer tetracycline (FIG. 2, panel b).

Construction of a tTA-Dependent Promoter. To generate promoters activatable by tTA, tetOs were inserted upstream of minimal promoter sequences. For $P_{hCMV}$ the upstream enhancer region was removed by PCR and a Xho I cleavage site was introduced adjacent to position −53. This minimal promoter, designated $P_{hCMV*}$, spans the original $P_{hCMV}$ sequence from +75 to −53 (+1 being the first nucleotide transcribed) and, in addition, contains a Stu I site around −31 (FIG. 1, panel b). tetO sequences were fused to this core promoter by insertions at the Xho I site (FIG. 1).

The tetO sequence O2 of Tn10 is a 19-bp inverted repeat to which tetR binds as a 46-kDa dimer (Hillen & Wissmann, "Topics in Molecular and Structural Biology," in *Protein-Nucleic Acid Interaction*, Saeger & Heinemann, eds., Macmillan, London, 1989, Vol. 10, pp. 143–162). It was chemically synthesized and ligated into the Xho I cleavage site of the polylinker located upstream of the minimal tk promoter in plasmid pT81-luc (Nordeen, S. K., *BioTechniques* 6:454–457 (1988)). Multiple insertions of tetOs created a set of promoters that contained between 1 and 7 tetO sequences upstream from position −81 of the tk promoter. A Xho I/Sal I fragment containing 7 tetOs fused head to tail was recovered from one of the constructs and transferred into the Xho I site upstream of $P_{hCMV*}$. Due to the asymmetry of the Xho I/Sal I fragment, two $P_{hCMV*}$-tetO constructs were obtained that differ in the distance between the operators and position +1 of $P_{hCMV}$, which is 95 bp for $P_{hCMV*-1}$ and 76 bp for $P_{hCMV*-2}$. The plasmids containing these promoters are designated pUHC13-3 and pUHC13-4, respectively (FIG. 1, panel b). When HeLa cells were transiently transfected with these plasmids, high levels of luciferase activity were monitored whenever the cells were cotransfected with pUHD15-1, which provided the coding sequence of tTA. Little activity was observed with cultures grown in the presence of tetracycline (1.0 µg/ml) or with plasmids containing $P_{hCMV*}$ only. Since $P_{hCMV*-1}$ and $P_{hCMV*-2}$ were activated by tTA to a significantly higher degree than any of the $P_{tk}$ constructs, the latter ones were not investigated further.

Quantitation of $P_{hCMV*-1}$ and $P_{hCMV*-2}$ Activation by tTA. To quantify the stimulation of $P_{hCMV*}$-tetO constructs by tTA, HeLa cell lines were established that contained the $P_{hCMV*-1}$ or the $P_{hCMV*-2}$-luciferase as well as the $P_{hCMV}$-tTA expression units stably integrated. Conditions for culturing and selecting cells have been described (Deuschle et al., *Proc. Natl. Acad. Sci. USA* 86:5400–5405 (1989)). In a first step cells were cotransfected with pUHD15-1 and pSV2neo (Southern & Berg, *J. Mol. Appl. Genet.* 1:327–341 (1982)). Clones resistant to G418 were assayed for transactivation of $P_{hCMV*-1}$ by transient transfection with pUHC13-3. In all HeLa cell clones in which the tetracycline-responsive promoters were active, tTA was not detectable by Western blots or by immunofluorescence. Its presence was just barely visible in electrophoretic mobility shift experiments of highly labeled tetO DNA. This indicates very low intracellular concentrations of tTA and may reflect a selection against squelching effects caused by higher concentrations of VP16-activating domains (Gill & Ptashne, *Nature (London)* 334:721–724 (1988)).

One of the positive clones, HtTA-1, was then cotransfected with a plasmid carrying the hygromycin-resistance gene (pHMR272; Bernard et al., *Exp. Cell Res.* 158:237–243 (1985)) and either pUHC13-3 or pUHC13-4, resulting in the X and T series of clones, respectively. Clones resistant to hygromycin and G418 were assayed for luciferase activity. As shown in Table 1, in the absence of tetracycline this activity differed in individual clones by almost four orders of magnitude. However, in all cases the luciferase activity was sensitive to tetracycline in the culture. This demonstrates that the expression of luciferase is dependent on the function of tTA, which obviously is capable of activating promoter constructs $P_{hCMV*-1}$ and $P_{hCMV*-2}$.

When the luciferase activity within various clones was monitored in the presence and absence of tetracycline hydrochloride (Sigma), two remarkable results emerged. (i) In all clones tested, tTA greatly stimulated promoter activity, even up to five orders of magnitude in clone XI. (ii) In clones T14, T16, X1 and X2 (Table 1), tetracycline reduced luciferase activity to values that cannot be quantified even at high protein concentration of extracts due to instrumental limitations (i.e., rlu/µg of protein ≦2). This demonstrates that $P_{hCMV*-1}$ and $P_{hCMV*-2}$ are virtually silent when integrated in the proper genomic environment and that their activity depends exclusively on the action of tTA.

The tTA inactivation studies were carried out with 1 µg of tetracycline per ml in the culture medium. A partial inactivation of tTA is, however, readily achieved with tetracycline concentrations below 0.1 µg/ml as shown in FIG. 3, panel a. In the two clones analyzed (T12 and X1), a stepwise reduction of the tetracycline concentration in the medium gradually increased the luciferase activity. These results again demonstrate that, in the case of clone X1, tTA can regulate transcriptional activity, as monitored by luciferase activity, by over five orders of magnitude. Moreover, at tetracycline concentrations sufficient for full inactivation of tTA (0.1 µg/ml), no change in growth behavior or morphology of HeLa cells occurs. Only at tetracycline concentrations well above 10 µg/ml were such changes observed upon prolonged incubation.

Kinetics of Tetracycline Action. The time course of tetracycline action was analyzed in cultures grown in the absence or presence of tetracycline. At time 0 the antibiotic was added to the tetracycline-free cultures (final concentration, 1 µg/ml), whereas the tetracycline-containing cultures were rinsed and incubated in fresh, antibiotic-free medium (FIG. 3, panel b). At various times cells were harvested and analyzed for luciferase activity. As shown in FIG. 3, panel b, the depletion of tetracycline leads to a rapid induction of luciferase activity, reaching >20% of the fully induced level within 12 hr. A similarly rapid reduction of luciferase activity was observed when tetracycline was added to the fully active tetracycline-free system: within 8 hr, activity dropped to about 10% and reached <2% of its original value after 12 hr.

The fusion of the Tn10-derived *E. coli* tetR with the activation domain of VP16 from HSV has generated a transactivator exhibiting all of the properties required for the specific and stringent regulation of an individual gene in a eucaryotic cell. The transactivator tTA produced in HeLa cells binds specifically to tetO sequences in vitro. This association is prevented by tetracycline. When bound to tetOs placed upstream of minimal promoters, tTA efficiently activates transcription from such promoters in vivo in a tetracycline-dependent manner. The transactivator is produced in HeLa cells in amounts sufficiently high for strong activation of transcription though low enough to avoid any detectable squelching effects (Gill & Ptashne, *Nature (London)* 334:721–724 (1988)).

The usefulness of heterologous regulatory systems as the one described here depends decisively on quantitative parameters such as the extent of inactivation and the efficiency of activation of gene expression as well as the kinetics of transition from one state to the other. For the tet system these parameters were measured in HeLa cell lines that constitutively express tTA and that also contain the luciferase gene stably integrated and under the control of tTA-dependent promoters. The clones characterized thus far express the luciferase gene to various extents. This is not surprising since differences in the integration sites and in the number of integrated transcription units would be expected. However, in all cases the expression of luciferase is sensitive to tetracycline. In some clones tetracycline has the most dramatic effect of reducing the luciferase activity from high levels over several orders of magnitude to background. This demonstrates that in HeLa cells the two promoters $P_{hCMV*-1}$ and $P_{hCMV*-2}$ have no measurable intrinsic activity. Their function strictly depends on tTA. The residual luciferase activity observed in some clones in the presence of tetracycline must therefore be due to position effects.

The tTA-dependent promoters can be kept in a partially activated state by low concentrations of tetracycline. As shown in FIG. 3, panel a, varying the tetracycline concentration between 0 and 0.1 µg/ml allows adjustment of promoter activity within a range of several orders of magnitude. This may allow assessment also of quantitative parameters of gene function in vivo.

The activation and inactivation of tTA by the antibiotic appears to be not only an efficient but also a rapid process. When cells from tetracycline containing medium are shifted to tetracycline-free medium, significant luciferase activity is induced within 4 hr and >20% of the steady-state level is reached within 12 hr after the shift. Interestingly, even the cultures that were only exposed to tetracycline-free medium during the washing procedure before reincubation in tetracycline-containing medium show a small but reproducible increase in luciferase activity that is still detectable after 4 hr (FIG. 3b).

When tetracycline is added to a culture of X1 cells, luciferase activity is reduced ≈10-fold within 8 hr and >50 fold within 12 hr. This decrease is remarkably fast if one takes into account the half-life of luciferase of around 3 hr reported for eucaryotic cells (measured by cycloheximide inhibition: Nguyen et al., *J. Biol. Chem.* 264:10487–10492 (1989); Thompson et al., *Gene* 103:171–177 (1991)) and indicates a rapid uptake of tetracycline by HeLa cells followed by a fast and efficient shutdown of transcription. Although the half-life of luciferase and its mRNA remains to be determined in this system, these conclusions are supported by observations in plant cells, where tetracycline inactivates tetR within <30 min (Gatz et al., *Mol. Gen. Genet* 227:229–237 (1991)).

Taken together, these dam show that tetracycline, unlike IPTG in a eukaryotic lacR/O-based system, is able to act fast in cultures of eucaryotic cells. The possibility of rapidly switching the activity of a tTA-dependent promoter not only is of interest in studying gene function itself but also should allow analysis of mRNA decay rates of individual genes under physiological conditions.

In clone X1 tetracycline reduces luciferase activity reproducibly by five orders of magnitude. This suggests that binding of tetracycline to tTA may lower the association constant between the transactivator and its operator to a much greater extent than that measured for tetR (Takahasi et al., *J. Mol. Biol.* 187:341–348 (1986)) and as described for IPTG in the lacR/O system, where the binding constant $k_{Ro}$ is reduced only 1000-fold by the inducer (Barkley and Bourgeois in *The Operon*, Miller and Reznikoff (eds.), Cold Spring Harbor Laboratory, Cold Spring Harbor, N.Y., 1980; pp. 177–220.)

On the other hand, the results obtained in transient experiments with minimal tk promoters fused to single, dimeric, and heptameric tetO sequences strongly suggest a synergistic effect of multiple tTA binding sites. The efficient inactivation of tTA by tetracycline is therefore most likely due to a large difference in the binding constants of tTA and tTA/tetracycline for the tetO and the nonlinear effect of tetracycline interfering with a cooperative process.

In conclusion, the results indicate that promoter-activating systems as described here are most promising for regulating individual genes in higher eukaryotic cells for several reasons. (i) For activators, in particular when acting through a cooperative mechanism, intracellular concentrations can be kept low, ensuring an efficient inactivation by the effector—in this case, tetracycline. By contrast, repressors in general complete directly with transcription factors and/or RNA polymerases for binding within a promoter region. In the absence of cooperativity, however, the window at which the repressor concentration is sufficiently high for tight expression but still low enough for efficient induction may be narrow and not easily adjustable in different systems. (ii) In an activating system as described here the synthesis of tTA can be driven by a tissue-specific promoter, whereas the tTA-dependent promoters are expected to function tissue independently, since they may require only general transcription factors in addition to tTA. By contrast, in a repressor-based system in which operators have to be placed within the context of a promoter sequence, an influence on promoter specificity cannot be excluded. (iii) The tet system offers specific advantages when compared to the intensely studied lac system. For example, tetR binds tetracycline much tighter ($k_a \approx 10^9$ $M^{-1}$; Takahashi et al., *J. Mol. Biol.* 187:341–348 (1986)) than lacR complexes IPTG ($k_a \approx 10^6$ $M^{-1}$; Barkley & Bourgeois in *The Operon*, Miller & Rezinkoff, eds., Cold Spring Harbor Lab., Cold Spring Harbor, N.Y., 1980, pp. 177–220). Thus, very low, nontoxic concentrations of tetracycline function effectively. Moreover, a large number of tetracycline analogues are known, of which some appear to have far superior properties as effectors than tetracycline itself. In this context, it is interesting to note that detailed information on the pharmacological properties of tetracycline, in particular pharmacokinetic parameters, is available, which will facilitate application of this system in transgenic animals.

From the foregoing description, one skilled in the art can easily ascertain the essential characteristics of this invention, and without departing from the spirit and scope thereof, can make various changes and modifications if the invention to adapt it to various usages and conditions without undue experimentation. All patents and publications cited herein are incorporated by reference in their entirety.

TABLE 1

Tetracycline-dependent Luciferase Activity of Different HeLa Cell Clones

| Clone | Luciferase activity, rlu/μ of protein | | Activation Factor |
|---|---|---|---|
|  | With Tc | Without Tc |  |
| T7  | 1074 ± 75 | 79,197 ± 2,119   | $7.3 \times 10^1$ |
| T11 | 2.5 ± 0.4 | 34,695 ± 1,127   | $1.3 \times 10^4$ |
| T12 | 3.5 ± 0.9 | 35,298 ± 5,009   | $1 \times 10^4$ |
| T14 | ≦2        | 33 ± 4           | $\geq 1.5 \times 10^1$ |
| T15 | 286 ± 47  | 49,070 ± 2,784   | $1.7 \times 10^2$ |
| T16 | <2        | 541 ± 133        | $\geq 2.7 \times 10^2$ |
| X1  | ≦2        | 257,081 ± 40,137 | $\geq 1 \times 10^5$ |
| X2  | ≦2        | 104,840 ± 20,833 | $\geq 5 \times 10^4$ |
| X7  | 75 ± 7    | 125,745 ± 18,204 | $1.6 \times 10^3$ |

The HeLa cell clone HtTA-1, which constitutively expresses tTA, was cotransfected with pUHC13-3 or pUHC13-4 and pHMR272. Hygromycin-resistant clones were examined for luciferase activity. Nine clones identified were subcloned and luciferase activity was quantified in the presence (1 μ/ml) and absence of tetracycline (Tc). Values are arithmetic means of three independent luciferase determinations (from three independently grown cultures). Luciferase activities of <2 rlu/μg of protein are too close to the instrumental background to be quantified.

What is claimed is:

1. A polynucleotide molecule coding for a transactivator fusion protein comprising a prokaryotic tet repressor and a eucaryotic transcriptional activator protein domain.

2. The polynucleotide molecule of claim 1, wherein said eucaryotic transcriptional activator protein domain comprises the C-terminal 130 amino acids of the virion protein 16 of herpes simplex virus.

3. The polynucleotide molecule of claim 1, further comprising an operably linked promoter.

4. The polynucleotide molecule of claim 3, wherein said promoter is constitutive in eucaryotic cells.

5. The polynucleotide molecule of claim 3, wherein said promoter is tissue specific.

6. The polynucleotide molecule of claim 3, wherein said promoter is developmentally regulated.

7. The polynucleotide molecule of claim 4, wherein said constitutive promoter is the human cytomegalovirus promoter IE.

8. The polynucleotide molecule of claim 4, wherein said constitutive promoter is the Tk promoter of HSV.

9. The polynucleotide of claim 1 which is DNA.

10. A polynucleotide molecule coding for a protein, wherein said polynucleotide is operably linked to a minimal promoter and at least one tet operator sequence.

11. The polynucleotide molecule of claim 10, wherein said minimal promoter spans the nucleotide sequences from position +75 to −53 or +75 to −31 of the cytomegalovirus promoter IE (+1 being the first nucleotide transcribed).

12. The polynucleotide of claim 10 or 11, comprising seven tet operator sequences.

13. A vector comprising the polynucleotide molecule of claim 1 or 10.

14. A eucaryotic cell transfected with the polynucleotide molecule of claim 1.

15. A eucaryotic cell transfected with the polynucleotide molecule of claim 10.

16. A eucaryotic cell transfected with (a) a first polynucleotide molecule coding for a transactivator fusion protein comprising a prokaryotic tet repressor and a eucaryotic transcriptional activator protein domain; and (b) a second polynucleotide molecule coding for a protein, wherein said second polynucleotide molecule is operably linked to a minimal promoter and at least one tet operator sequence.

17. A method to decrease or shut off the expression of a heterologous protein coded for by the second polynucleotide of claim 16, comprising cultivating the eucaryotic cell of claim 16 in a medium comprising tetracycline or a tetracycline analogue.

18. A kit comprising a carrier means having in close confinement therein at least two container means, wherein a first container means contains a first polynucleotide molecule coding for a transactivator fusion protein comprising a prokaryotic tet repressor and a eucaryotic transcriptional activator protein domain, and a second container means contains a second polynucleotide molecule comprising a minimal promoter operably linked to at least one tet operator sequence, wherein said minimal promoter is capable of being ligated to a heterologous gene sequence coding for a polypeptide.

19. A kit comprising a carrier means having in close confinement therein at least two container means, wherein a first container means contains a eucaryotic cell transfected with a first polynucleotide molecule coding for a transactivator fusion protein comprising a prokaryotic tet repressor and a eucaryotic transcriptional activator protein domain, and a second container means contains a second polynucleotide molecule comprising a minimal promoter operably linked to at least one tet operator sequence, wherein said minimal promoter is capable of being ligated to a heterologous gene sequence coding for a polypeptide.

* * * * *